United States Patent
Rizzo et al.

(10) Patent No.: US 11,957,413 B2
(45) Date of Patent: Apr. 16, 2024

(54) SOLITARY WAVE-BASED TRANS-LID TONOMETER

(71) Applicant: University of Pittsburgh—Of the Commonwealth System of Higher Education, Pittsburgh, PA (US)

(72) Inventors: Piervincenzo Rizzo, Pittsburgh, PA (US); Amir Nasrollahi, Pittsburgh, PA (US); Samuel Dickerson, Pittsburgh, PA (US); Ritesh Misra, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 812 days.

(21) Appl. No.: 16/987,020

(22) Filed: Aug. 6, 2020

(65) Prior Publication Data

US 2021/0038078 A1 Feb. 11, 2021

Related U.S. Application Data

(60) Provisional application No. 62/883,296, filed on Aug. 6, 2019.

(51) Int. Cl.
*A61B 5/00* (2006.01)
*A61B 3/16* (2006.01)

(52) U.S. Cl.
CPC ........ *A61B 3/16* (2013.01); *A61B 2562/0223* (2013.01)

(58) Field of Classification Search
CPC .... A61B 3/16; A61B 2562/0223; A61B 3/165
See application file for complete search history.

(56) References Cited

U.S. PATENT DOCUMENTS

| | | | | |
|---|---|---|---|---|
| 4,860,755 A | * | 8/1989 | Erath | A61B 3/16 600/405 |
| 4,883,056 A | * | 11/1989 | Langham | A61B 3/16 600/398 |
| 4,951,671 A | * | 8/1990 | Coan | A61B 3/16 600/587 |

(Continued)

OTHER PUBLICATIONS

Bagheri et al., "Assessing the pressure of tennis balls using non-linear solitary waves: a numerical study," *Sports Eng.*, 20:53-62 (Mar. 2017).

(Continued)

*Primary Examiner* — May A Abouelela
(74) *Attorney, Agent, or Firm* — Klarquist Sparkman, LLP

(57) ABSTRACT

Apparatus include a particle array configured to propagate an incident solitary wave to an eye, a housing configured to support the particle array, and a sensor coupled to the particle array and configured to detect a return solitary wave propagating along the particle array from the eye. Methods include directing an incident solitary wave along a solitary wave particle array coupled to an eye and detecting a return solitary wave propagating along the solitary wave particle array from the eye. Methods also include estimating intraocular pressure for the eye by comparing solitary wave data to a relationship between a time of return solitary wave time of flight and an intraocular pressure.

21 Claims, 27 Drawing Sheets

(56) References Cited

U.S. PATENT DOCUMENTS

| | | | | |
|---|---|---|---|---|
| 5,165,409 | A * | 11/1992 | Coan | A61B 3/16 600/401 |
| 5,546,941 | A * | 8/1996 | Zeimer | A61B 3/16 600/404 |
| 8,894,578 | B2 * | 11/2014 | Wong | A61B 5/6846 600/398 |
| 9,155,467 | B1 * | 10/2015 | Enikov | A61B 3/16 |
| 11,006,828 | B2 * | 5/2021 | Bitoun | A61B 3/165 |
| 2004/0230124 | A1 * | 11/2004 | Querfurth | A61B 5/031 600/485 |
| 2005/0020896 | A1 * | 1/2005 | Fuller | A61B 3/1005 600/405 |
| 2007/0156079 | A1 * | 7/2007 | Brown | A61B 3/16 604/9 |
| 2008/0103381 | A1 * | 5/2008 | Kontiola | A61B 3/16 600/405 |
| 2008/0208146 | A1 * | 8/2008 | Brandwein | A61B 5/14514 604/272 |
| 2009/0270711 | A1 * | 10/2009 | Jarvin | A61B 3/16 600/398 |
| 2009/0275819 | A1 * | 11/2009 | Miwa | A61B 3/165 600/399 |
| 2009/0275820 | A1 * | 11/2009 | Miwa | A61B 3/0041 600/399 |
| 2011/0054291 | A1 * | 3/2011 | Enikov | A61B 3/16 600/405 |
| 2011/0275923 | A1 * | 11/2011 | Glovinsky | A61B 3/0083 600/398 |
| 2012/0296261 | A1 * | 11/2012 | Whitaker | A61F 9/0008 604/20 |
| 2015/0160088 | A1 * | 6/2015 | Wu | A61B 3/16 73/700 |
| 2016/0174838 | A1 * | 6/2016 | Herranen | A61B 3/16 351/246 |
| 2016/0270656 | A1 * | 9/2016 | Samec | A61B 3/1216 |
| 2018/0296090 | A1 * | 10/2018 | McCafferty | A61B 3/107 |
| 2019/0150736 | A1 * | 5/2019 | Wallace | G16H 20/13 |
| 2019/0239753 | A1 * | 8/2019 | Wentz | H01J 31/501 |
| 2019/0380577 | A1 * | 12/2019 | Martin | A61B 3/0025 |
| 2020/0196864 | A1 * | 6/2020 | Martin | A61B 3/16 |
| 2020/0390331 | A1 * | 12/2020 | Schweitzer | A61B 3/16 |
| 2021/0113151 | A1 * | 4/2021 | Vilser | G16H 30/40 |
| 2021/0145278 | A1 * | 5/2021 | Von Bünau | A61B 3/16 |
| 2021/0154201 | A1 * | 5/2021 | Verkman | A61P 27/04 |
| 2021/0244528 | A1 * | 8/2021 | Balaji | C08F 214/262 |
| 2021/0251569 | A1 * | 8/2021 | Salkola | A61B 5/0053 |

OTHER PUBLICATIONS

Misra et al., "Wireless Module for Nondestructive Testing/Structural Health Monitoring Applications Based on Solitary Waves," Sensors, 18 pages (May 26, 2020).

Nasrollahi et al., "Numerical and Experimental Study on the Dynamic Interaction Between Highly Nonlinear Solitary Waves and Pressurized Balls," Journal of Applied Mechanics, 85:031007-01-031007-11 (Mar. 2018).

Nasrollahi et al., "Solitary Waves to Assess the Internal Pressure and the Rubber Degradation of Tennis Balls," Experimental Mechanics, 59(1):65-77 (Jan. 2019).

Dabasia, et al., "Evaluation of a new rebound tonometer for self-measurement of intraocular pressure," British Journal of Ophthalmology, 100(8)bjophthalmol-2015-307674 (Nov. 2015).

Heijl et al., "Reduction of Intraocular Pressure and Glaucoma Progression: Results from the Early Manifest Glaucoma Trial," Archives of Ophthalmology, 120(10):1268-1279 (Oct. 2002).

Jóhannesson, "Intraocular pressure—clinical aspects and new measurement methods," Ph.D. dissertation Umea University, Sweden 58 pages (2011).

Kniestedt, et al., "Tonometry Through the Ages," Survey of Ophthalmology, 53(6):568-591 (Nov.-Dec. 2008).

Lee, et al., "Effect of Different Head Positions in Lateral Decubitus Posture on Intraocular Pressure in Treated Patients With Open-Angle Glaucoma," American Journal of Ophthalmology, 160(5):929-936 (Nov. 2015).

Mudie et al., "The Icare Home (TA022) Study: Performance of an Intraocular Pressure Measuring Device for Self-Tonometry by Glaucoma Patients," Ophthalmology, 123(8):1675-1684 (Aug. 2016).

Nasrollahi, et al., "A Nondestructive Evaluation Approach to Characterize Tennis Balls," Journal of Nondestructive Evaluation, Diagnostics and Prognostics of Engineering Systems, 2(1):011004-011011 (Feb. 2019).

Nasrollahi et al., "Modeling a new dynamic approach to measure intraocular pressure with solitary waves," Journal of the Mechanical Behavior of Biomedical Materials, 103:103534 (Mar. 2020).

"Terminology and Guidelines for Glaucoma," European Glaucoma Society, 4th Edition, 72 pages (Jun. 2014).

Troost et al., Deviations between transpalpebral tonometry using TGDc-01 and Goldmann applanation tonometry depending on the IOP level, Graefe's Archive for Clinical Experimental Ophthalmology, 243:853-858 (Mar. 15, 2005).

Van der Jagt et al., "Three portable tonometers, the TGDc-01, the Icare and the Tonopen XL, compared with each other and with Goldmann applanation tonometry," Ophthalmic and Physiological Optics, 25(5):429-435 (Oct. 2005).

Yung et al., "An overview of home tonometry and telemetry for intraocular pressure monitoring in humans," Graefe's Archive for Clinical and Experimental Ophthalmology, 252(8):1179-1188 (May 2014).

* cited by examiner

SOLITARY WAVE-BASED TRANS-LID TONOMETER

CROSS REFERENCE TO RELATED APPLICATION

This application claims priority to U.S. Provisional Patent Application No. 62/883,296, filed Aug. 6, 2019, and is incorporated by reference herein.

FIELD

The field is tonometry.

BACKGROUND

Glaucoma is an age-related disease affecting the optic nerve and is the second leading cause of blindness in the world. Eye pressure is known to be a major risk factor for glaucoma. When the balance between the fluid production and drainage inside the eye is abnormal the intraocular pressure (IOP) increases, raising the risk of developing glaucoma.

In the U.S., nearly 9 million visits are made each year for the diagnosis or treatment of glaucoma but still, a significant fraction of glaucoma cases remains undiagnosed because the symptoms do not appear until significant damage occurs to the eye. According to the National Eye Institute (NEI): (1) women are more affected than men (61% vs. 39%); (2) the annual cost to the government is over $1.5B in health care expenditures, lost income tax revenues, and Social Security benefits; (3) by 2050 the number of people in the U.S. with glaucoma will almost triple. Worldwide, glaucoma affect ~4% of the population and 70+ million people have the disease without knowing it.

The measurement of IOP is the cornerstone of the diagnosis and management of glaucoma, as the elevated value of this pressure is the only risk factor that can be modified by proper therapy or surgical intervention. Unfortunately, IOP follows a circadian rhythm and fluctuates throughout the day. For this reason, a single office-based measurement is typically insufficient to discover daily changes and spikes, nor can they demonstrate the effect of medication or patients' compliance to a given therapy. Similar to diabetics measuring blood glucose levels, clinical evidence suggests that multiple daily measurements would be beneficial. However, this is possible only with an off-the-counter hand-held device that patients of any literacy and fair dexterity can self-administer. To satisfy these characteristics, the IOP measurement device should be easy-to-use, inexpensive, and not require sterilization or topical anesthesia, by way of example. Thus, a need remain for improved devices, such as ones that can include one or more of these advantages, and which are not currently available to glaucoma patients.

SUMMARY

According to aspects of the disclosed technology, apparatus and methods measure intraocular pressure of an eye through the use of solitary waves.

According to an aspect of the disclosed technology, apparatus include a particle array configured to propagate an incident solitary wave to an eye, a housing configured to support the particle array, and a sensor coupled to the particle array and configured to detect a return solitary wave propagating along the particle array from the eye. In some examples, the particle array comprises a plurality of adjacently arranged loosely coupled particles that propagate the incident and return solitary waves from one particle to the next. Some examples further include a particle array compressive member coupled to at least one of the particles to provide a compression for the particle array contact among the particles. In some examples, the particle array compressive member comprises a spring and/or magnet. In some examples, the housing includes a bend defining a bent path for the particle array. In some examples, the bent path is arranged such that a weight of a plurality of the particles along a portion of the bent path compress the particles to provide the loose coupling. In some examples, the particles have spherical, cylindrical, or elliptical shape, or a mix of shapes. In some examples, the particles are made of PTFE, steel, or another material having an elastic modulus between 0.01 and 200 GPa. In some examples, the sensor comprises a magnetic coil encircling at least a portion of at least one of the particles. In some examples, the sensor comprises a piezoelectric transducer embedded in at least one of the particles. In some examples, the sensor comprises a stress wave sensor. In some examples, the sensor comprises a piezoelectric transducer embedded between a pair of disks. Some examples include a membrane attached to the housing, and configured to removably contact the eyelid to couple the particle array to the eye. Some examples include an actuator coupled to the particle array and configured to produce the incident solitary wave in the particle array. Some examples include circuitry configured to drive the actuator, to filter solitary wave data detected by the sensor, and to sample the filtered solitary wave data. Some examples include circuitry configured to wirelessly transmit the filtered solitary wave data to a separate computing device. In some examples, the driving circuitry includes delay circuitry configured to reduce a sampling error. In some examples, the filter circuitry is configured to provide a cutoff frequency configured to reduce a delay associated with a phase lag. In some examples, the actuator comprises a solenoid configured to raise a striker particle and to drop the striker particle from a height. Some examples include a function generator coupled to the actuator and configured to generate an incident solitary wave signal for the actuator, and a digitizer coupled to the sensor and configured to digitize the detected return solitary wave to form a digitized return solitary wave signal. Some examples include a processor coupled to the digitizer and function generator, and a memory coupled to the processor and configured with instructions executable by the processor for controlling the generation of the incident solitary wave in the particle array. In some examples the memory is further configured with instructions for determining an intraocular pressure of an eye based on one or more characteristics of the digitized return solitary wave signal. Some examples include a communication node coupled to the processor and configured to communicate data describing the digitized return solitary wave signal to an external signal processing device. In some examples, the external signal processing device is a mobile device and the communication node is a wireless communication node. In some examples, the actuator comprises an electromagnet and striker, and the function generator comprises a switching circuit. In some examples, the housing has a pen-shape grippable by a user against an eyelid of the user.

According to another aspect of the disclosed technology, methods include directing an incident solitary wave along a solitary wave particle array coupled to an eye and detecting at least one return solitary wave propagating along the solitary wave particle array from the eye. Some examples estimate an intraocular pressure of the eye by comparing detected characteristics of the return solitary wave to characteristics of the incident solitary wave. Some examples estimate an intraocular pressure of an eye by comparing solitary wave data associated with a tonometry eye measurement to a relationship between a time of return solitary wave time of flight and/or a ratio of incident and detected wave amplitudes and an intraocular pressure.

According to another aspect of the disclosed technology, computer-readable media including stored instructions which, when executed by one or more computing devices, cause the computing devices to estimate intraocular pressure for an eye by comparing stored solitary wave data describing a tonometer detection event of the eye including return solitary wave data to a relationship between solitary waves and an intraocular pressure. Some examples include stored instructions causing the computing devices to direct an actuator to produce an incident solitary wave along a solitary wave particle array coupled to the eye, and to store the solitary wave data including data from a detection signal received in response to the actuating.

According to another aspect of the disclosed technology, apparatus include at least one processor and memory configured with instructions executable by at least one processor to estimate an intraocular pressure of an eye by comparing solitary wave data associated with a tonometry eye measurement to a relationship between a solitary wave characteristics and intraocular pressure.

The foregoing and other objects, features, and advantages of the disclosed technology will become more apparent from the following detailed description, which proceeds with reference to the accompanying figures.

DETAILED DESCRIPTION

Figure 1:
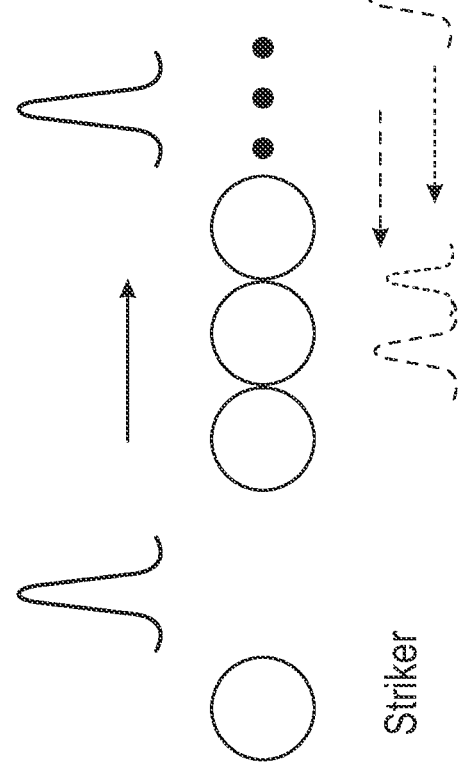
FIG. 1 is a schematic of a solitary wave tonometry operation.
Figure 1:
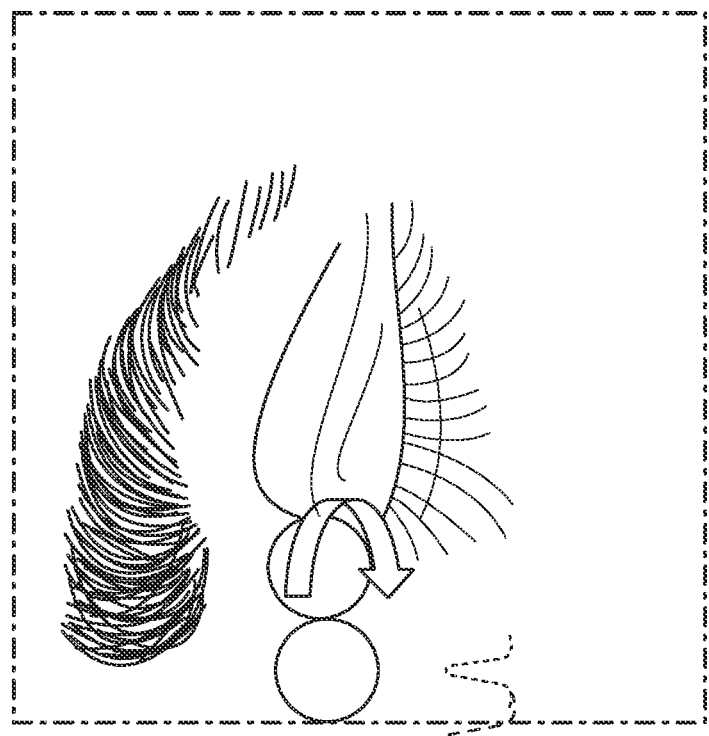
Figure 2:
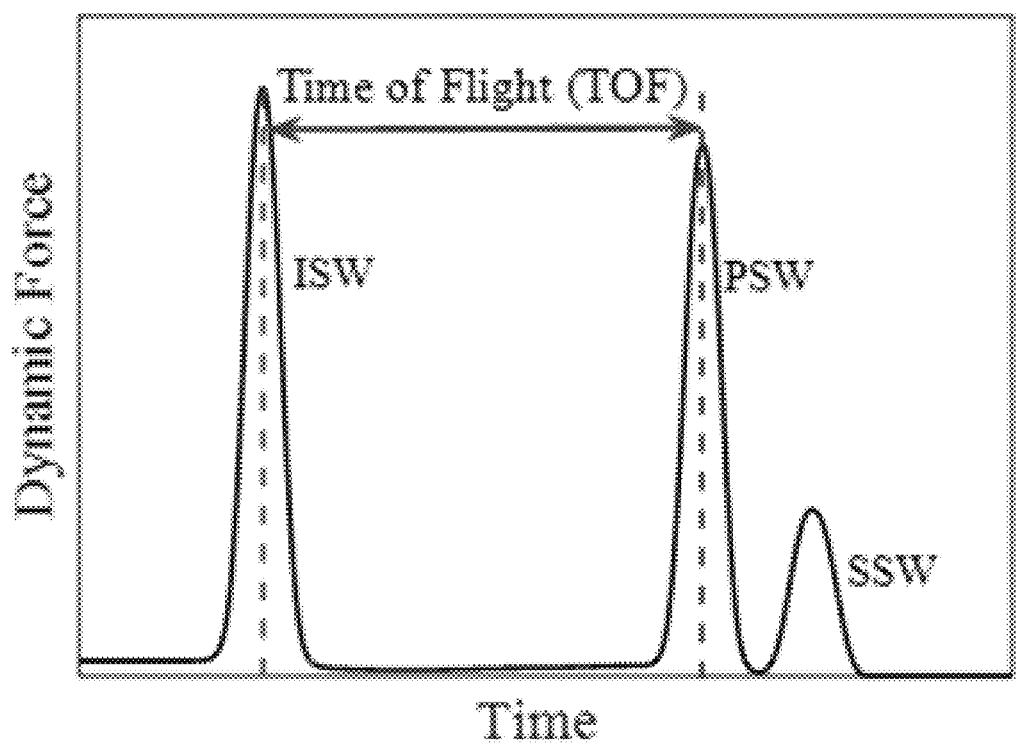
FIG. 2 is a graph of dynamic force with respect to time for a tonometry measurement.

Examples herein include a new smart healthcare solution to enable the early detection and the proper treatment of glaucoma by enabling frequent measurements of the intraocular pressure (IOP). The engineering principle of various representative examples is shown in FIG. 1. A chain of a few mm small particles is in contact with the lid of the eye to be diagnosed. An incident solitary wave (ISW) is induced at one end (such as mechanically and/or electrically, e.g., with a striker or actuator), propagates along the chain, and reaches the eye (e.g., by propagating through an eyelid); here the single pulse is reflected back to the chain originating one or more reflected waves. Shown in FIG. 2 are example amplitude traces of the ISW (moving towards the eyelid) and the first of typically two reflected pulses, with the two reflected pulses hereinafter being referred to as the primary and secondary reflected waves (PSW and SSW), generated at the interface with the eyelid, are shown in FIG. 2. The amplitude and travel time of the reflected pulses are dependent on the eye pressure. In some examples, the dependence can occur irrespective of the cornea thickness and/or eyelid stiffness (or an IOP dependence on cornea thickness and/or eyelid stiffness can be controlled through calibration). Because of this, representative device embodiments can be placed in contact with the eyelid of the eye to be measured, thereby enabling any patient to self-administer a tonometry test to capture, store, and transmit wirelessly the physiological state of their eye pressure. In further examples, a device surface can directly contact the sclera.

Representative Examples

Elevated IOP is one of the major risk factors for the development and progression of glaucoma. [Heijl, A., Leske, M. C., Bengtsson, B., Hyman, L., Bengtsson, B., & Hussein, M. (2002). Reduction of intraocular pressure and glaucoma progression: results from the Early Manifest Glaucoma Trial. Archives of ophthalmology, 120(10), 1268-1279]. Accurate assessment of IOP is important because elevated IOP is the only risk factor that can be modified by therapeutic interventions [Lee, T. E., Yoo, C., Lin, S. C., &

Kim, Y. Y. (2015). Effect of different head positions in lateral decubitus posture on intraocular pressure in treated patients with open-angle glaucoma. *American journal of ophthalmology*, 160(5), 929-936]. The fact that IOP follows a circadian rhythm and is also subjected to spontaneous changes throughout the day, makes office-based single measurements neither sufficient to discover daily changes and spikes, nor valid to demonstrate the effect of medication or patients' compliance to a given therapy. As such, frequent daily measurements would be ideal, similar to diabetics measuring blood glucose levels. However, this is possible only with an off-the-counter hand-held not-sticking device that patients of any literacy and fair dexterity can self-administer. To satisfy these characteristics, the device should be easy-to-use, inexpensive, and should not require sterilization or topical anesthesia. However, absent examples disclosed herein, such a device does not exist. Several methods exist for the measurement of IOP; however, none of them has the features described above. Thus, some representative examples of the disclosed technology herein can fill this gap and can (a) use of the propagation of highly nonlinear solitary waves (HNSWs) for the measurement of IOP; (b) provide a portable easy-to-use device that patients of any age and fair dexterity can self-administer; and (c) use simple though effective signal processing to link solitary waves to IOP. Exemplary devices and methods can contribute to development of a new generation of instruments to be used in eye care.

The relatedness between pressure and solitary waves was tested on tennis balls. In these tests, a device based on the similar engineering principle of the measurement of intraocular pressure was used to measure the internal pressure of tennis balls. In examples herein, the engineering principles at work for tennis balls is applied to work on human (or other animal) eyeballs. Experiments on tennis balls were conducted in a laboratory setting and the results were published in (1) Nasrollahi, A., Lucht, R., and Rizzo, P. (2019). "Solitary waves to assess the internal pressure and the rubber degradation of tennis balls" *Experimental Mechanics*, 59(1), 65-77. DOI: DOI 10.1007/s11340-018-0432-1; (2) Nasrollahi, A., Sefa Orak, M., Kosinski, K., James, A., Weighardt, L., and Rizzo, P. (2019). *"An NDE approach to characterize tennis balls,"* ASME Journal of Nondestructive Evaluation, Diagnostics and Prognostics of Engineering Systems, 2, 011004-1, (8 pages); (3) Nasrollahi, A., Rizzo, P., and Sefa Orak, M. (2018) "Numerical and experimental study of the dynamic interaction between highly nonlinear solitary waves and pressurized balls," *ASME Journal of Applied Mechanics*, 85(3), 031007-1 031007-11; and (4) Bagheri, A., and Rizzo, P. (2017) "Assessing the pressure of tennis balls using nonlinear solitary waves: a numerical study," *Sports Engineering*, 20(1), 53-62, all of which being incorporated by reference herein.

The effectiveness of various examples of the disclosed technology (including methods) can be evaluated through in vitro and in vivo trials, and various example devices can be designed and assembled to form portable devices, which can be tested in clinical trials.

Tonometry

Methods of measuring IOP can be clustered in three large groups: palpation, manometry, and tonometry [1]. Palpation is the oldest, simplest, least expensive, and least accurate method. It consists of displacing the redundant skin of the upper eyelid and balloting alternatively the central meridian of the globe with the tips of each index finger [1]. Manometry is the most precise and the most invasive approach because a hollow needle is surgically inserted into the anterior chamber. Manometry provides the reference pressure by which all other methods should be judged. It is mainly used in laboratory and its use in living human eyes is restricted to eyes undergoing enucleation or intraocular surgery [1]. Tonometry is based on the relationship between IOP and the force necessary to deform the cornea by a given amount [2]. Among the three groups, tonometry is the preferred approach because it is not invasive as manometry and is more accurate than palpation.

Tonometers can be sub-grouped in applanation, rebound, and indentation, and correspond to the physical principles of tonometers applied in clinical practice today. The gold standard for measuring IOP is the Goldmann Applanation Tonometer (GAT) against which any other methods are judged and compared. GAT is based on the Imbert-Fick principle IOP=F/A, which states that the IOP is proportional to the force F needed to applanate a pre-defined area A [3,4]. However, this law is only applicable to an infinitely thin membrane perfectly elastic, dry, and flexible [3-5]. In reality, none of these assumptions applies to applanation of the cornea, which has variable curvature, has finite thickness, is not perfectly elastic, is coated by the tear film, and is a small part of the overall larger-diameter eyeball, which is connected via the limbus to the sclera. GAT requires the use of a drop of anesthetic and fluorescein, must be proctored by a health care professional, and must be administered with the patient in a sitting position [5].

Rebound tonometers are ballistic devices that measure the return-bounce motion of an object impacting the cornea [1]. ICare is the most widely used rebound tonometer. It mounts a single-use probe that exchanged after every patient; the probe is propelled against the cornea, impacts with it and rebounds from the eye. Individual measurements are digitally displayed, and after six consecutive measurements the average and the standard deviation are given [6]. On thick corneas, Icare overestimates IOP even more than GAT. Intersessional repeatability of IOP taken with the Icare is poorer than with GAT. Icare also developed Icare HOME for self-tonometry. However, a 2016 study [7] concluded that: "Not all participants could learn how to use the Icare HOME device, but for those who could, [ . . . ] nearly 1 in 6 individuals may fail to certify in use of the device based on large differences in IOP when comparing GAT with the Icare HOME measurements". Finally, this device was not approved by the FDA.

TonoPen is a hybrid applanation/indentation system in which a tip is covered by a disposable latex cover and applied perpendicularly to indent an anesthetized cornea. Owing to the requirements for a localized anesthesia, this device cannot be proctored home and need to be administered by an eye care professional. Each measurement requires several applanations. An acceptable applanation is indicated by an audible click after contact with the cornea. A microprocessor averages the acceptable waveforms and gives a digital readout of IOP. TonoPen gives higher readings than GAT, and above 21 mmHg it underestimates GAT readings.

The tonometer TGDc-01 is a device designed to measure the IOP through the eyelids without anesthesia. The movement of a small rod falling freely onto the eyelid surface is measured. Individual measurements are displayed digitally. Three measurements are usually performed [6]. Troost et al. proved that TGDc-01 underestimates the IOP when compared with GAT [1,8-10]. Deviations between the TGDc-01 and the GAT were found to be clinically relevant and therefore TGDc-01 could not be considered as an alternative to GAT [7-6]. There is also the uncomfortable sensation for the patient of the rod tapping the eyelid.

Yung et al. [11] reviewed the technologies for self-tonometry and for continuous monitoring of IOP currently undergoing development and clinical trials: portable devices, contact lenses, and telemetry using implantable pressure sensors. Besides the invasive nature of these solutions, some of their conclusions were: "[ . . . ], no effective method of 24-hour IOP monitoring currently exists outside of office visits. Current portable devices for IOP measurement have not been shown to be reliable for home use by patients, and have not yet yielded accurate results compared to GAT. These devices are still at the research stage and do not have any commercial name yet.

Various tonometry examples of the disclosed technology herein may resemble the rebound tonometry in some respects. However, representative examples herein do not require tapping, impacting, or applanating the cornea, do not require topical anesthesia, and/or do not require trained health care professionals to make reliable measurements. Tonometry References [1]-[11] Referenced Above 1 C. Kniestedt, O. Punjabi, S. Lin, and R. L. Stamper (2008). "Tonometry Through the Ages", *Survey of Ophthalmology*, 53(6), 568-591.
2 European Glaucoma Society, *Terminology and guidelines for glaucoma*, 4th Edition, June 2014.
3 Goldmann H (1957): Applanation tonometry. New York. Josiah Macy, Jr. Foundation
4 Goldmann H, Schmidt T (1957) "Applanation Tonometry," *Ophthalmologica*, 134(4), 221-242.
5 Jóhannesson, G. (2011). *Intraocular pressure—clinical aspects and new measurement methods*, Ph.D. dissertation Umea University, Sweden.
6 Liane H. Van Der Jagt, Nomdo M. Jansonius (2005). "Three portable tonometers, the TGDc-01, the ICARE and the Tonopen XL, compared with each other and with Goldmann applanation tonometry," *Ophthalmic and Physiological Optics*, 25(5), 429-435.
7 Mudie, L. I., LaBarre, S., Varadaraj, V., Karakus, S., Onnela, J., Munoz, B., and Friedman, D. S. (2016). The Icare HOME (TA022) Study: Performance of an Intraocular Pressure Measuring Device for Self-Tonometry by Glaucoma Patients. *Ophthalmology*.
8 Dabasia, P. L., Lawrenson, J. G., and Murdoch, I. E. (2015). Evaluation of a new rebound tonometer for self-measurement of intraocular pressure. *British Journal of Ophthalmology*,
9 Müller A, Godenschweger L, Lang G E, et al. (2004). "Prospective comparison of the new indentation tonometer TGdC-01, the non-contact tonometer PT100 and the conventional Goldmann applanation tonometer," *Klin Monatsbl Augenheilkd*, 221, 762-768.
10 Troost A, Specht K, Krummenauer F, et al. (2005). "Deviations between transpalpebral tonometry using TGDc-01 and Goldmann applanation tonometry depending on the IOP level," *Graefes Arch Clin Exp Ophthalmol*, 243, 853-858.
11 Yung, E., Trubnik, V., and Katz, L. J. (2014). An overview of home tonometry and telemetry for intraocular pressure monitoring in humans. *Graefe's Archive for Clinical and Experimental Ophthalmology*, 252(8), 1179-1188.

Solitary Wave-Based Tonometry Measurement Models and Experiments

The following description relates to the article by Nasrollahi and Rizzo "Modeling a New Dynamic Approach to Measure Intraocular Pressure with Solitary Waves," *Journal of the Mechanical Behavior of Biomedical Materials*, 103, March 2020, 103534, https://doi.org/10.1016/j.jmbbm.2019.103534, and which is incorporated by reference herein.

A conceptually novel tonometer is proposed based on engineering principles never explored in ophthalmology, and the principles are schematized in FIG. 1. A short granular chain made of a few mm spherical particles, hereinafter referred to as the chain, is in point-contact with the lid of the eye to be diagnosed. The particles support the propagation of highly nonlinear solitary waves (HNSWs), which are a special kind of stress waves fundamentally different than those waves typically encountered in acoustics and ultrasound. Those waves are characterized by having a return force linearly dependent on the displacement. HNSWs are instead nonlinear: the return force F is nonlinearly proportional to the displacement from equilibrium according to the Hertz's law $F=A_b\delta^{3/2}$. Here $\delta$ is the indentation between two adjacent identical interacting beads, and $A_b$ is the contact stiffness equal to $[E_b(2R_b)^{0.5}]/[3(1-v_b^2)]$ where $E_b$, $R_b$, and $v_b$ are the beads modulus, radius, and Poisson's ratio, respectively. HNSWs are also unique with respect to conventional linear waves because their intrinsic tunability makes them useful for a wide range of engineering applications, including but not limited to nondestructive evaluation (NDE), energy harvesting, and impact mitigation. A typical time waveform of these pulses is shown in FIG. 2 where an incident solitary wave (ISW) is induced at one end by the mechanical impact of a striker. The incident wave propagates along the chain of spherical particles, and reaches the eyelid. As discussed further below, this single pulse gives rise to two reflected pulses, the primary and the secondary reflected solitary waves (PSW and SSW). The research hypothesis investigated in the feasibility study was that the amplitude and time-of-flight (ToF) of these reflected pulses are monotonically dependent on the eye pressure. However, in various tonometry device examples herein, wave features that can be included in the analysis to identify or estimate IOP can include but are not limited to amplitudes of the three waves (ISW, PSW, SSW), the time of flight of the PSW and/or SSW, the width at half amplitude of each of the three waves, and any declination in terms of their ratios or product, such as the ratio of the amplitude of the PSW to the amplitude of the ISW or the product of the two amplitudes, by way of example.

Recently, HNSWs were used to characterize tennis balls and their internal pressure. A finite element model was modified and coupled to a discrete particle model to describe the dynamic interplay between the solitary waves and submillimeter soft material (the human cornea) under varying pressure. Parameters such as the internal pressure and the geometric and mechanical properties of the chain were varied in order to investigate the effect of these characteristics on the sensitivity of new tonometer instruments.

In analyzing underlying engineering principles and applications to ophthalmology, the mechanical interaction between solitary waves and thin walled soft materials was investigated. The ability of the waves to be used to measure internal pressure was assessed and the feasibility of solitary wave-based tonometer devices was also explored. Further examples were developed that can provide non-invasive tonometry applications based on solitary waves.

The following description presents a finite element formulation developed to predict the dynamical interaction between the waves and the cornea. The model was adapted from existing models to measure the internal pressure of tennis balls in order to account for the geometric and mechanical properties of the cornea. A spring-mass model is coupled to the finite element formulation to describe the propagation of the solitary waves along the chain. Also, a numerical setup was described to quantify the effects of the internal pressure on some selected features of the solitary waves, along with related numerical results.

Figure 3:
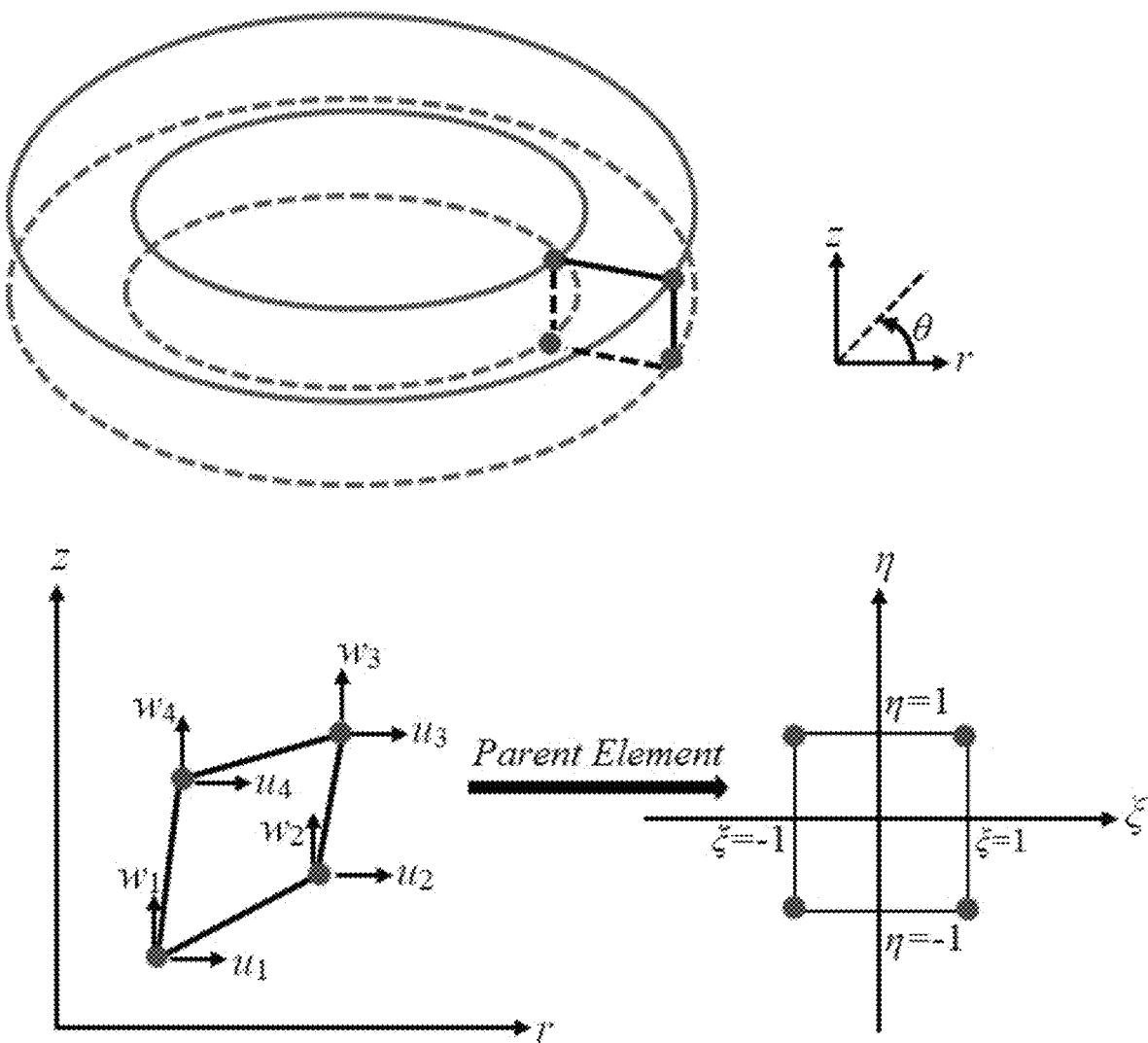
FIG. 3 is a perspective view and graph associated with four-node quadrilateral isoparametric finite elements used in modeling solitary-wave based tonometry.

A four-node quadrilateral axisymmetric element was used. As shown in FIG. 3, each node had one degree of freedom u in the radial direction $r(\zeta, \eta)$ ($u_1$, $u_2$, $u_3$, $u_4$) and one degree of freedom w in the vertical direction $z(\zeta, \eta)$ ($w_1$, $w_2$, $w_3$, $w_4$). Due to the axisymmetric nature of the problem, the Cauchy stress vector and the strain vector were $\underline{\sigma}=[\sigma_r\ \sigma_z\ \sigma_\theta\ \tau_{rz}]^T$ and $\underline{\varepsilon}=[\varepsilon_r\ \varepsilon_z\ \varepsilon_\theta\ \varepsilon_{rz}]^T$, respectively. This implied that for each element, there were three normal stresses/strains in the radial, vertical, and angular directions and one shear stress/strain in the radial-vertical direction). The material stiffness matrix $K^{mat}$ of the element was determined:

$$K^{mat} = 2\pi \int_{-1}^{1}\int_{-1}^{1}(B^T(\zeta,\eta)\cdot C\cdot B(\zeta,\eta)r(\zeta,\eta) \quad (1)$$
$$\det J(\zeta_i,\eta_j))d\zeta d\eta$$
$$\cong 2\pi \sum_{i=1}^{m}\sum_{j=1}^{n} w_{ij}B^T(\zeta_i,\eta_j)\cdot C\cdot B(\zeta_i,\eta_j)r(\zeta_i,\eta_j)$$
$$\det J(\zeta_i,\eta_j)$$

where m and n is the number of Gaussian points in $\zeta$ and $\eta$ directions, respectively, used in the numerical integration, $w_{ij}$ are the weight coefficients, $J(\zeta, \eta)$ is the Jacobian matrix, and $B(\zeta, \eta)$ is the strain-displacement matrix used to compute the strains $\varepsilon$ at any point inside the element using the nodal displacement vector d as:

$$\varepsilon = B^T \cdot d \quad (2)$$

Figure 4:
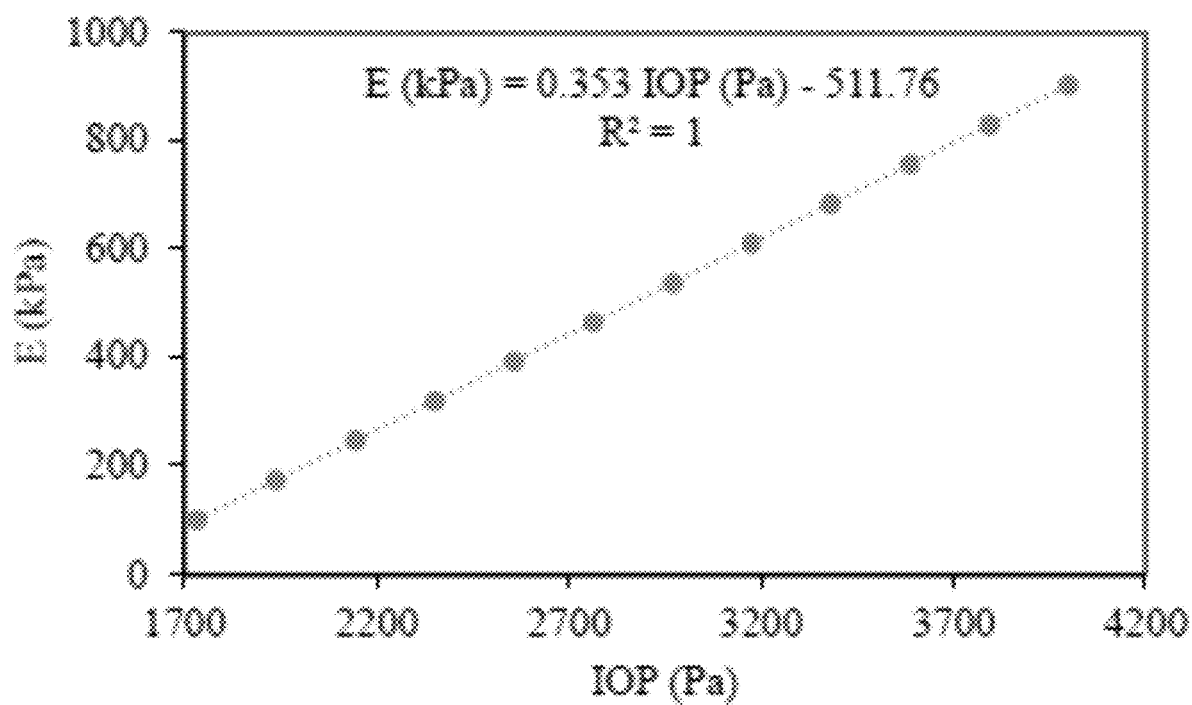
FIG. 4 is a graph showing a potential relationship between Young's modulus and an internal pressure (IOP) of the human cornea under certain eye properties.

Furthermore, Eq. (1) contains the stress-strain matrix C, which for a linear-elastic isotropic material equals to:

$$C = \frac{E}{(1+\nu)(1-2\nu)}\begin{bmatrix} 1-\nu & \nu & \nu & 0 \\ \nu & 1-\nu & \nu & 0 \\ \nu & \nu & 1-\nu & 0 \\ 0 & 0 & 0 & (1-2\nu)/2 \end{bmatrix} \quad (3)$$

where E is the Young's modulus and $\nu$ is the Poisson's ratio of the cornea. In some examples, the modulus of the human cornea can be considered as a linear function of the IOP, such as shown in FIG. 4. As such, Eq. (3) takes into account the internal pressure of the eye by updating the value of the Young's modulus of the cornea. However, this does not generally represent an impediment in a clinical setting where the IOP is the parameter to be measured. In various examples, other relations between IOP and solitary wave characteristics can be obtained and used to make IOP measurements with solitary waves.

The stress $\sigma$ and the consequent strain $\varepsilon$ generated by the internal pressure were treated as initial parameters in the eye. Thus, the geometric $K^{geo}$ and the total stiffness K were proportional to the internal pressure. The geometric nonlinear stiffness matrix $K^{geo}$ was given by [7]:

$$K^{geo} = 2\pi \int_{-1}^{1}\int_{-1}^{1}(\beta^T(\zeta,\eta)\cdot\sigma\cdot\beta(\zeta,\eta)r(\zeta,\eta) \quad (4)$$
$$\det J(\zeta_i,\eta_j))d\zeta d\eta$$
$$\cong 2\pi \sum_{i=1}^{m}\sum_{j=1}^{n} w_{ij}\beta^T(\zeta_i,\eta_j)\cdot\sigma\cdot\beta(\zeta_i,\eta_j)r(\zeta_i,\eta_j)$$
$$\det J(\zeta_i,\eta_j)$$

where $\beta$ contains the derivatives of the shape functions. The total stiffness of the cornea was the sum of the material stiffness matrix and the geometric nonlinear stiffness matrix, i.e.:

$$K = K^{mat} + K^{geo} \quad (5)$$

Finally, the mass matrix M and the load vector f for each element were given by:

$$M = 2\pi\rho\int_{-1}^{1}\int_{-1}^{1}(N^T(\zeta,\eta)r(\zeta,\eta)\ \det J(\zeta_i,\eta_j))d\zeta d\eta \quad (6)$$
$$\cong 2\pi\rho\sum_{i=1}^{m}\sum_{j=1}^{n} w_{ij}N^T(\zeta_i,\eta_j)r(\zeta_i,\eta_j)\ \det J(\zeta_i,\eta_j)$$

$$f = 2\pi\int_{-1}^{1}\int_{-1}^{1}\left(N^T(\zeta,\eta)\begin{Bmatrix} T_x(\zeta,\eta) \\ T_y(\zeta,\eta) \end{Bmatrix}r(\zeta,\eta)\ \det J(\zeta_i,\eta_j)\right)d\zeta d\eta \quad (7)$$
$$\cong 2\pi\sum_{i=1}^{m}\sum_{j=1}^{n} w_{ij}N^T(\zeta_i,\eta_j)\begin{Bmatrix} T_x(\zeta,\eta) \\ T_y(\zeta,\eta) \end{Bmatrix}r(\zeta_i,\eta_j)\ \det J(\zeta_i,\eta_j)$$

where $N(\zeta, \eta)$ is the shape functions vector in isoparametric (natural) coordinates, $\rho$ is the density of the material, $T_x$ and $T_y$ are the tractions along x and y directions, respectively, which can represent the components of the internal pressure along x and y, respectively, in some examples.

To obtain the stiffness and mass matrices as well as the load vector of the whole cornea, K, M and f were computed for each element of the mesh and then assembled using the connectivity matrix, formulated by implementing the advancing front method.

Figure 5:
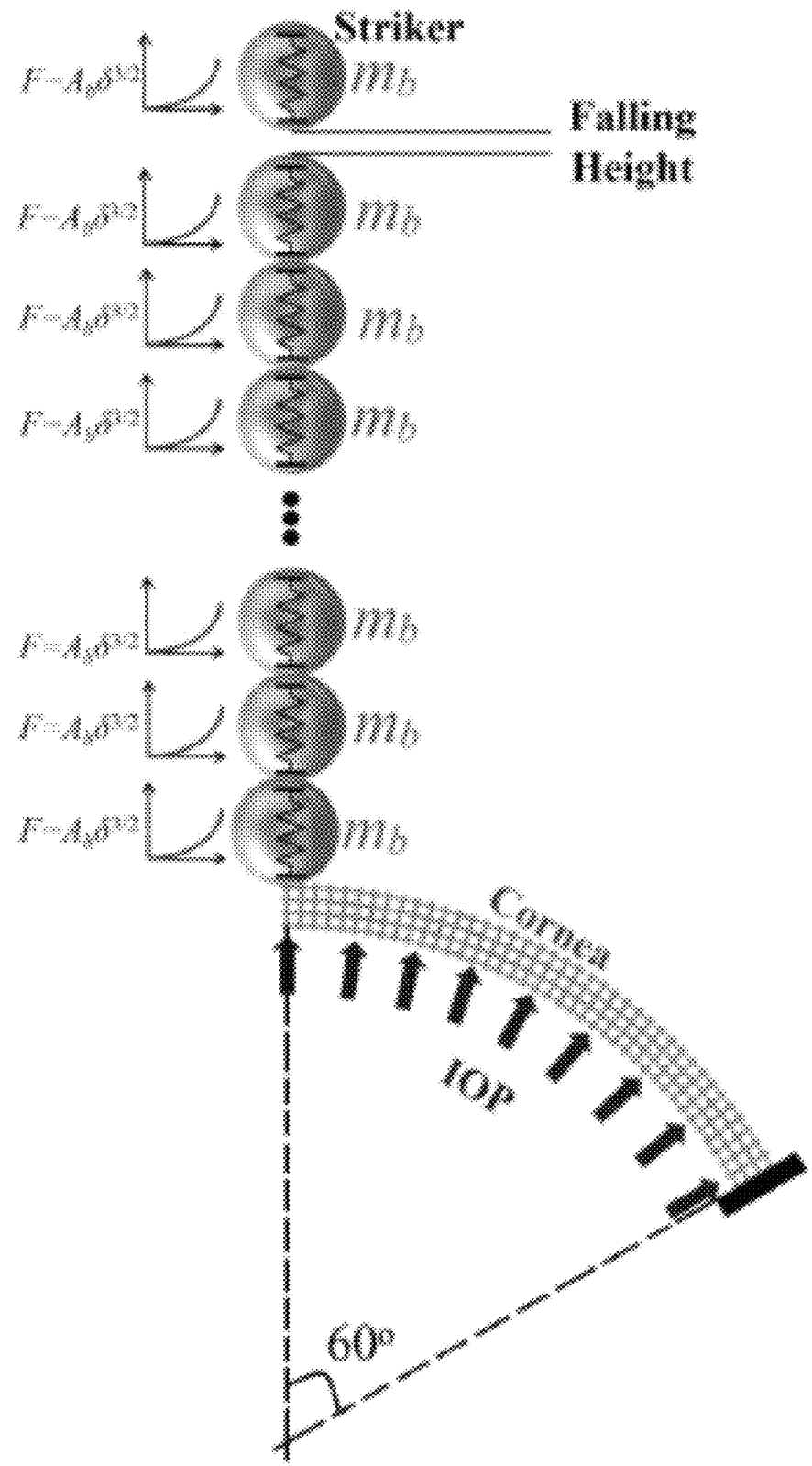
FIG. 5 is a schematic representation of a finite element model of a chain of spheres, supporting the propagation of a solitary wave, in contact with a human cornea.
Figure 6A:
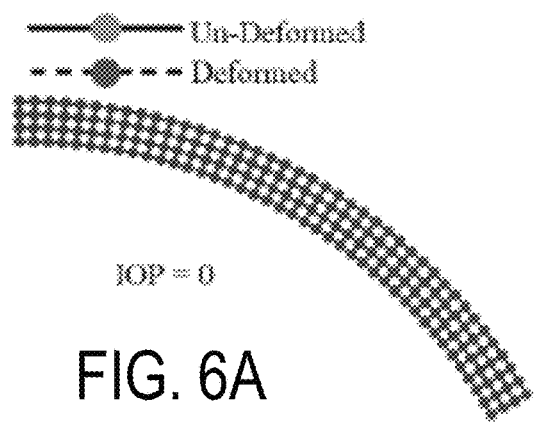
FIGS. 6A-6D are finite element model-based side views of a human cornea showing deformation at different intraocular pressures (IOPs), magnified by a factor of 20,000 for clarity.
Figure 6B:
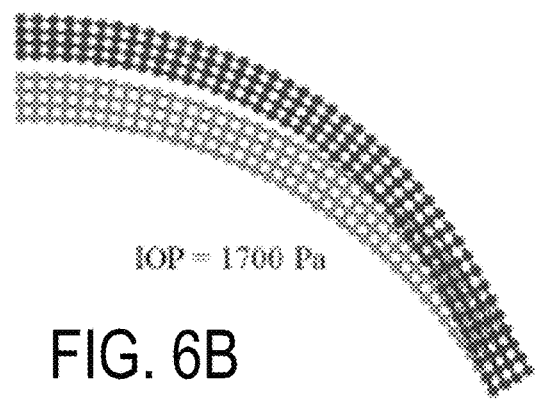
Figure 6C:
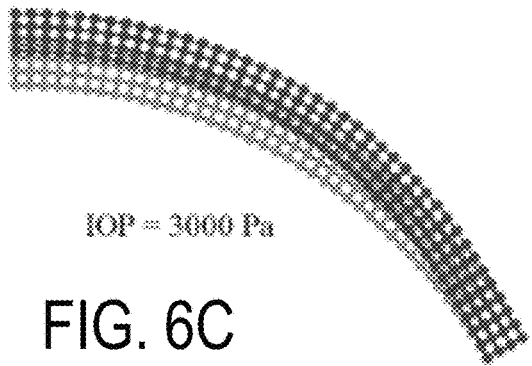
Figure 6D:
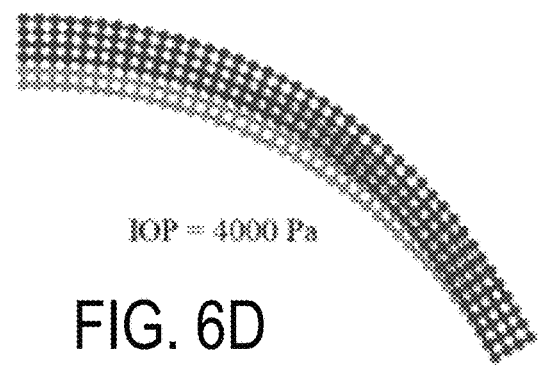

As stated above, the above finite element formulation was coupled to a discrete mass/spring model to predict the effect of the IOP on the propagation of the solitary waves inside the chain made of N spheres (FIG. 5). The second Newton's law was applied to the displacement $u_i(t)$ of the $i^{th}$ particle of mass mb yielding to the following set of differential equations of motion:

$$\ddot{u}_1(t) = \frac{A_b}{m_b}[u_2(t) - u_1(t)]_+^{3/2} - g \quad (8a)$$

$$\ddot{u}_i = \frac{A_b}{m_b}[u_{i+1}(t) - u_i(t)]_+^{3/2} - \frac{A_b}{m_b}[u_i(t) - u_{i-1}(t)]_+^{3/2} - g, \quad (8b)$$
$$i = 2, 3, \ldots, N-1$$

$$\ddot{u}_1(t) = \frac{A_c}{m_b}[u_{M,c}(t) - u_N(t)]_+^{3/2} - \frac{A_b}{m_b}[u_N(t) - u_{N-1}(t)]_+^{3/2} - g \quad (8c)$$

In Eq. (8), the first particle (i=1) represents the striker whose motion triggers the formation of the incident wave. The last particle (i=N) is instead the bead in contact with the eye to be evaluated. Furthermore, g is the gravity, $[x]_+$ means max(x,0), $u_{Mc}$ is the displacement of the cornea along the direction of the wave propagation, and $A_c$ is the contact stiffness at the cornea/bead interface. This Hertzian contact stiffness was obtained by dividing the magnitude of the load, applied at the contact point, to the corresponding displacement. Eq. (8) contains the Hertzian contact stiffness $A_b$ between two adjacent beads that, as mentioned hereinabove, is equal to:

$$A_b = \frac{E_b\sqrt{2R_b}}{3(1-\nu_b^2)} \quad (9)$$

For the cornea, the equation of motion was computed as:

$$\ddot{u}(t)=M_{rg}^{-1} \cdot f_{rg}(t)-(M_{rg}^{-1} \cdot K_{rg}) \cdot u(t) \quad (10)$$

where $M_{rg}$, $K_{rg}$, and $f_{rg}(t)$ are, respectively, the reduced global mass and stiffness matrices and the reduced global force vector, all obtained after applying the boundary conditions. $f_{rg}(t)$ includes static force due to the internal pressure and dynamic force of the HNSW. Displacements of the beads and the cornea were obtained by solving simultaneously Eqs. (8) and (10). These displacements were replaced into the Hertz's contact law:

$$f_1(t)=A_b[u_2(t)-u_1(t)]_+^{3/2} \quad (11a)$$

$$f_i=1/2(A_b[u_{i+1}(t)-u_i(t)]_+^{3/2}-A_b[u_i(t)-u_{i-1}(t)]_+^{3/2}),\ i=2, 3,\ldots,N-1 \quad (11b)$$

$$f_n(t)=1/2(A_c[u_{M,c}(t)-u_N(t)]_+^{3/2}-A_b[u_N(t)-u_{N-1}(t)]_+^{3/2}) \quad (11c)$$

to determine the dynamic force at each bead of the chain.

The cornea of healthy young adults (22-29 year-old) was considered. A circle sector of 7.8 mm radius and central angle equal to 120° was modeled. Owing to the axisymmetric nature of the physical phenomena being investigated, the geometry of the finite element model is shown in FIG. 5. The thickness, density and Poisson's ratio of the cornea were equal to 0.536 mm, 1000 kg/m3 and 0.49, respectively. As shown in FIG. 4, the Young's modulus of the cornea can be understood as a function of the eye pressure. Ten IOPs were considered ranging from 12.75 mmHg (1700 Pa) to 30.00 mmHg (4000 Pa) at step of 1.725 mmHg (230 Pa). Across this range, the cornea's modulus varied between 90 kPa and 900 kPa (FIG. 4). However, various modulus relations can depend on conditions and eye characteristics, and thus disclosed examples are not limited to the specific relations shown.

The mesh and the boundary conditions shown in FIG. 5 were considered. An advancing-front method was coded in MATLAB to mesh the cornea. The mesh consisted of 320 elements, 80 elements along the arc length and 4 elements along the radial direction, i.e. across the thickness. A Gaussian elimination method was used for the static analysis of the cornea under internal pressure and a built-in simultaneous 4-5th-order Runge-Kutta command in MATLAB (ode45) was employed to analyze the propagation of the solitary pulses along the chain placed in contact with the cornea.

Four chains made of twenty particles were considered in order to find the characteristics (diameter and modulus) of the particles that would provide the highest sensitivity of the solitary waves to the IOP variation. Two particles diameter, namely d=1 mm and 2 mm, and two materials, namely stainless steel and polytetrafluoroethylene (PTFE), were considered. For the steel: $E_b$=200 GPa, $v_b$=0.3, and $\rho_b$=7,850 kg/m³; for the PTFE: $E_b$=0.5 GPa, $v_b$=0.46, and $\rho_b$=2,200 kg/m³. Using Eq. (11b) the force amplitude of the pulses traveling through the tenth particle was measured. In this feasibility study, the tonometer was assumed to be in the vertical position. To mimic the free fall of the striker 1 mm above the chain, the initial velocity of the topmost sphere was set equal to 0.14 m/s. The numerical sampling frequency was equal to 2 MHz.

FIGS. 6A-6D shows the deformation of the cornea under four different internal pressures. For clarity, the deformation was magnified 20,000 times. The deformation under 12.75 mm Hg (1700 Pa) was the largest. This counterintuitive outcome is due to the increase of the Young's modulus with the internal pressure: as the cornea becomes stiffer with the increase in pressure, the deformation becomes smaller.

The chain was then placed on the strained cornea as showed in FIG. 5. The weight of the chain deformed the cornea further, but such deformation was about 4.5 μm for the 2 mm-PTFE beads case, i.e. much smaller than the one caused by the eye pressure. As such, the self-weight of the proposed tonometer has no adverse effects on the patients' eye.

As discussed above, in experiments, an incident wave was triggered by setting the initial velocity of the striker to 0.14 m/s. The waveforms associated with the four chains are shown in FIGS. 7A-7D when the IOP was equal to 12.75 mm Hg (1700 Pa). One significant feature of HNSWs not observed in linear waves, is that their phase velocity $V_s$ is directly proportional to the force amplitude $F_m$ as $V_s \sim F_m^{1/6}$, i.e. stronger pulses propagate faster. Another feature is that a solitary pulse can be engineered by tuning the mechanical and/or the geometric properties of the particles, including varying static precompression of the particles, to attain the desired wavelength, speed, and amplitude. These are seen in the arrival time and amplitude of the ISW in FIGS. 7A-7D: the dynamic force associated with the 2 mm steel spheres is about four-fold the force measured in the 1 mm steel spheres, and about two orders of magnitude higher than the 1 mm PTFE chain. Also, at a given particles' diameter, the arrival time of the ISW is proportional to the Young's modulus, and at a given material is inversely proportional to the particles' diameter. The time waveforms presented in FIGS. 7A-7D also reveal that regardless the size and modulus of the particles, two reflected pulses (the PSW and the SSW) are generated and their amplitude, time of flight, and duration depend on the properties of the beads. The duration of the pulse is a parameter called "contact time": the bigger and softer the particles, the wider are the pulses. Softer beads deform more and delay the response time to the load generated by the adjacent beads. Further, the contact time $T_c$ is a function of the velocity $V_s$, mass $m_b$, and contact stiffness $A_b$ according to: $T_c \approx 3.218 m_b^{2/5} V_s^{-1/5} A_b^{-2/5}$.

Figure 7A:
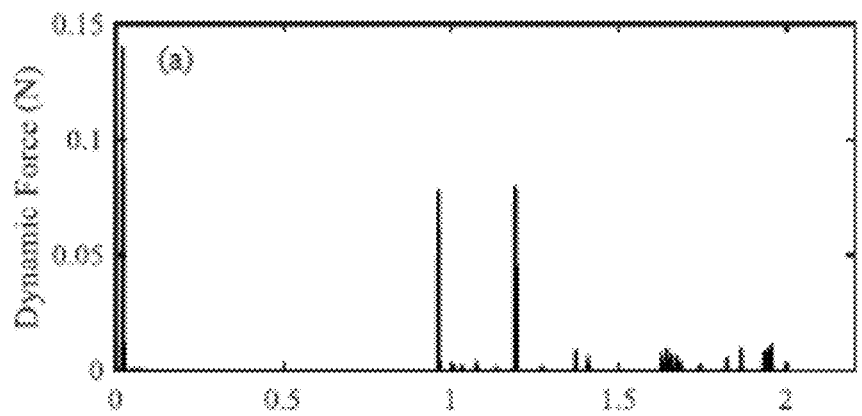
FIGS. 7A-7D are graphs of time waveforms associated with a 1 mm steel chain (i.e., a chain of spherical steel particles, each having a 1 mm diameter), a 2 mm steel chain, a 1 mm PTFE chain, and a 2 mm PTFE chain, respectively, recorded at a center of a 10th particle of respective 20-bead chains.
Figure 7B:
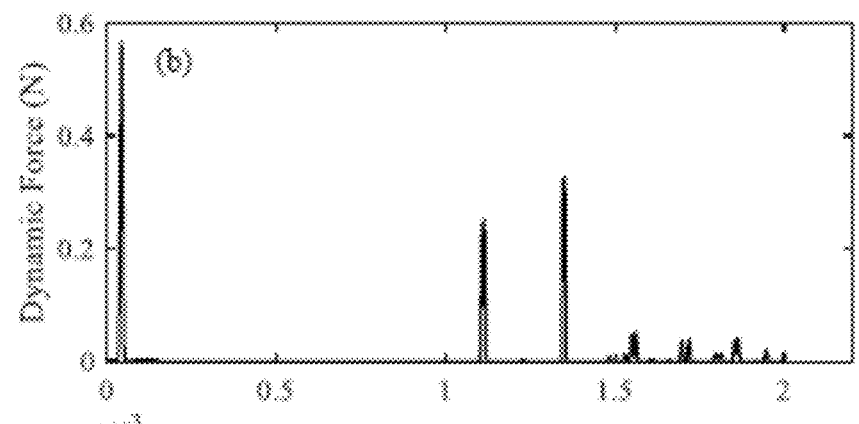
Figure 7C:
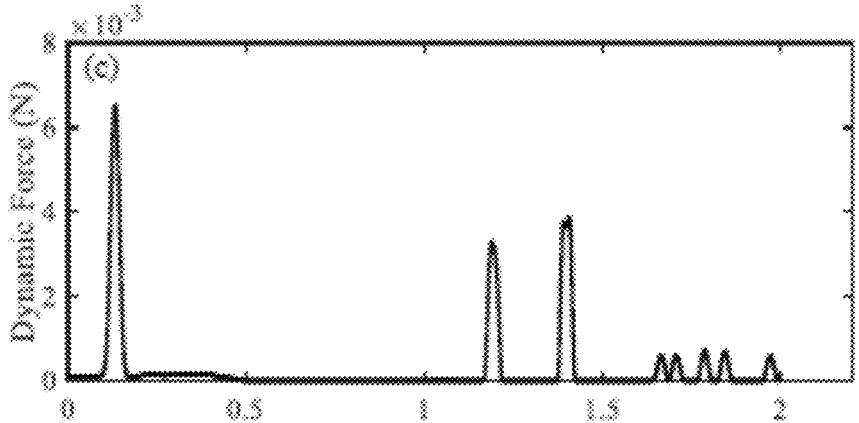
Figure 7D:
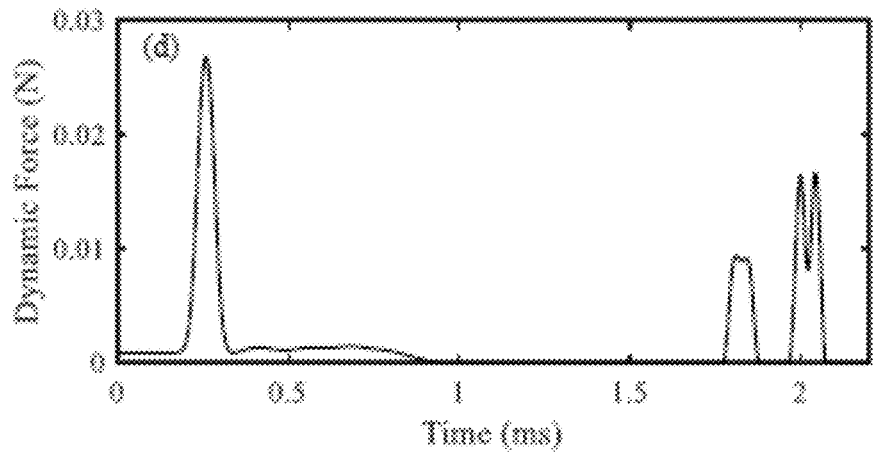
Figure 8A:
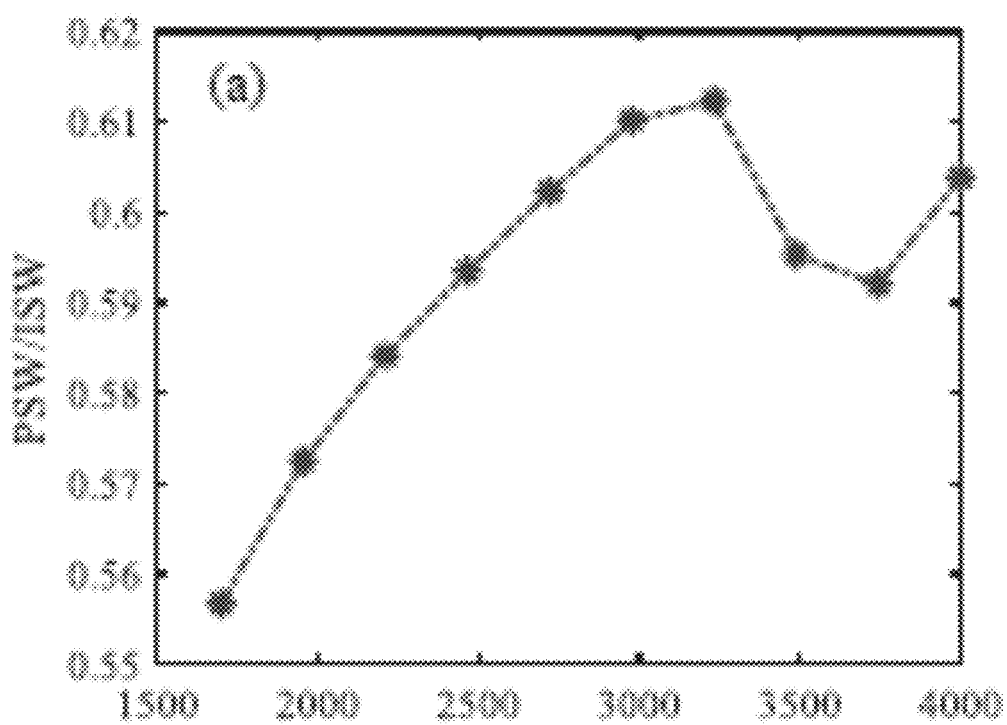
FIGS. 8A-8D are graphs of normalized amplitudes of a primary reflected solitary wave associated with the 1 mm steel chain, the 2 mm steel chain, the 1 mm PTFE chain, and the 2 mm PTFE chain, respectively.
Figure 8B:
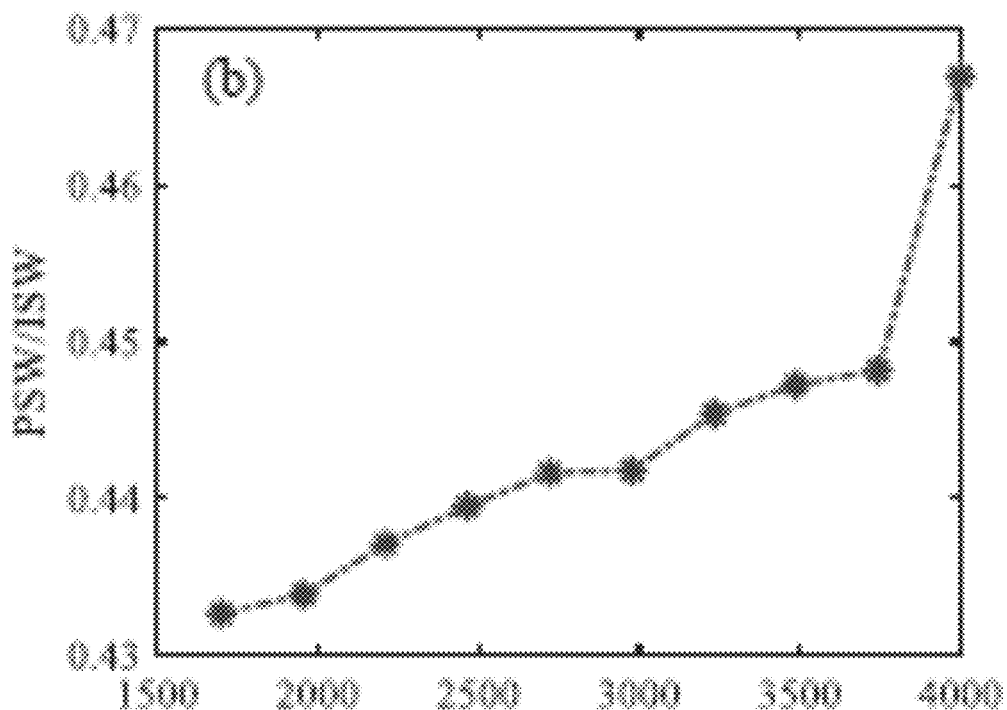
Figure 8C:
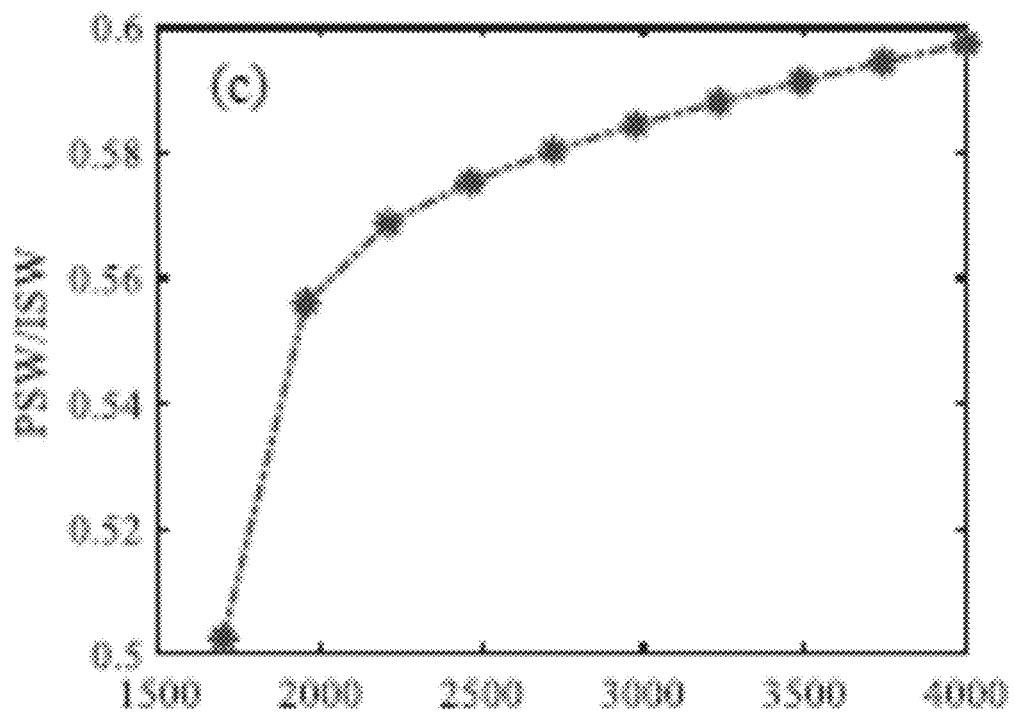
Figure 8D:
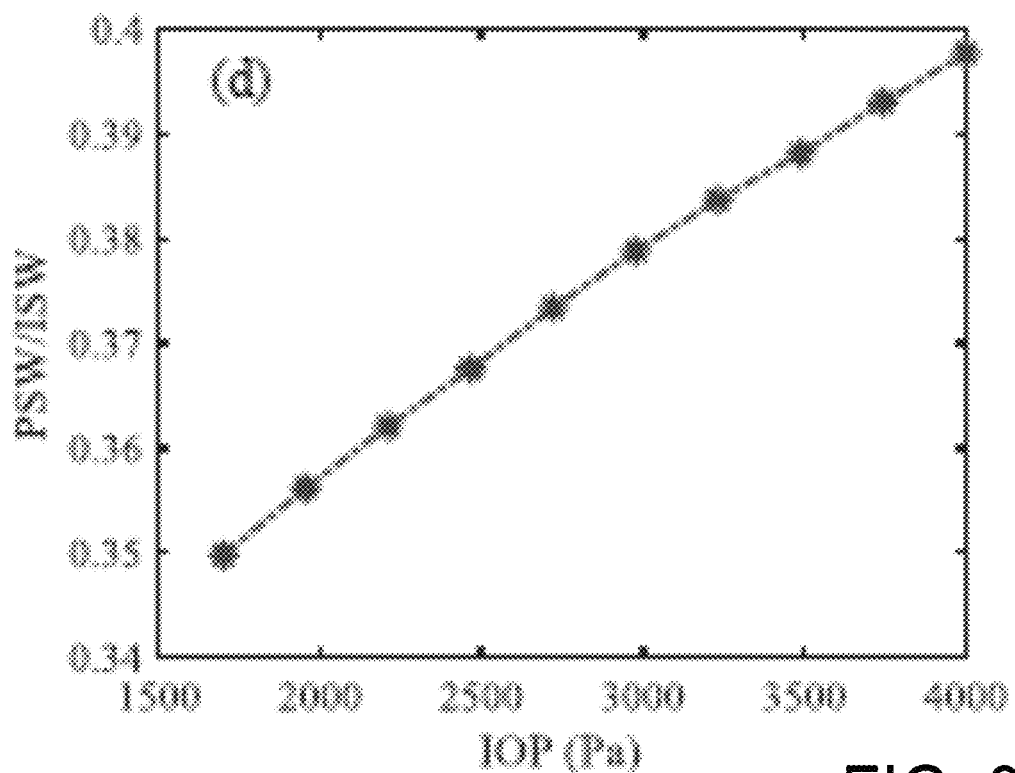
Figure 9A:
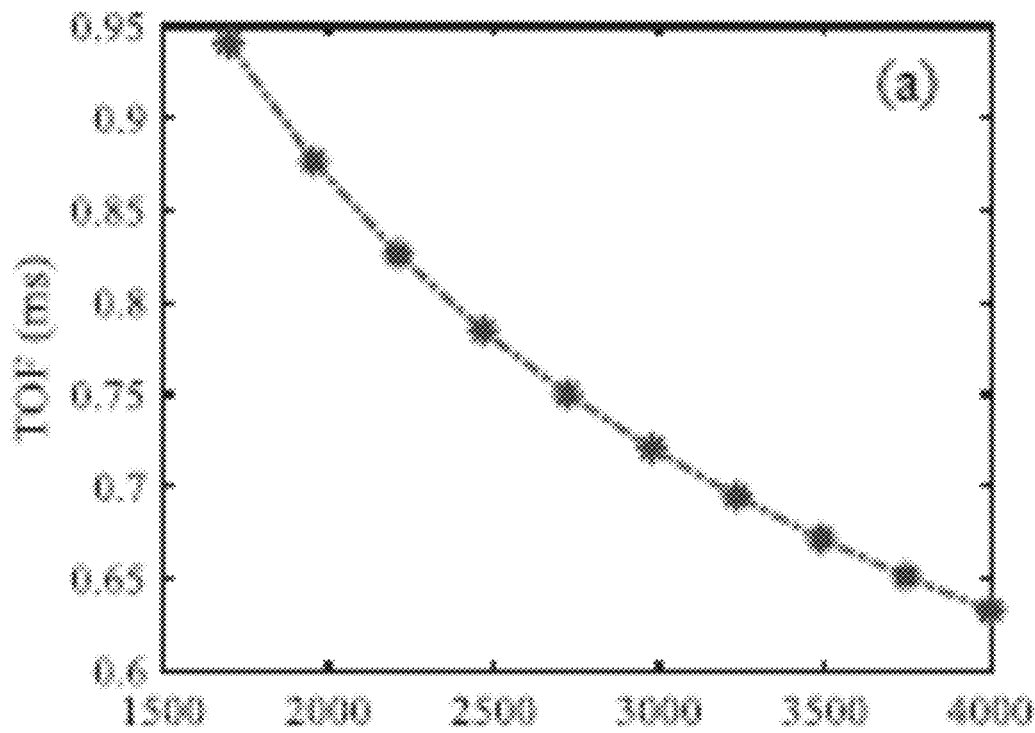
FIGS. 9A-9D are graphs of time of flight of solitary waves associated with the 1 mm steel chain, the 2 mm steel chain, the 1 mm PTFE chain, and the 2 mm PTFE chain, respectively.
Figure 9B:
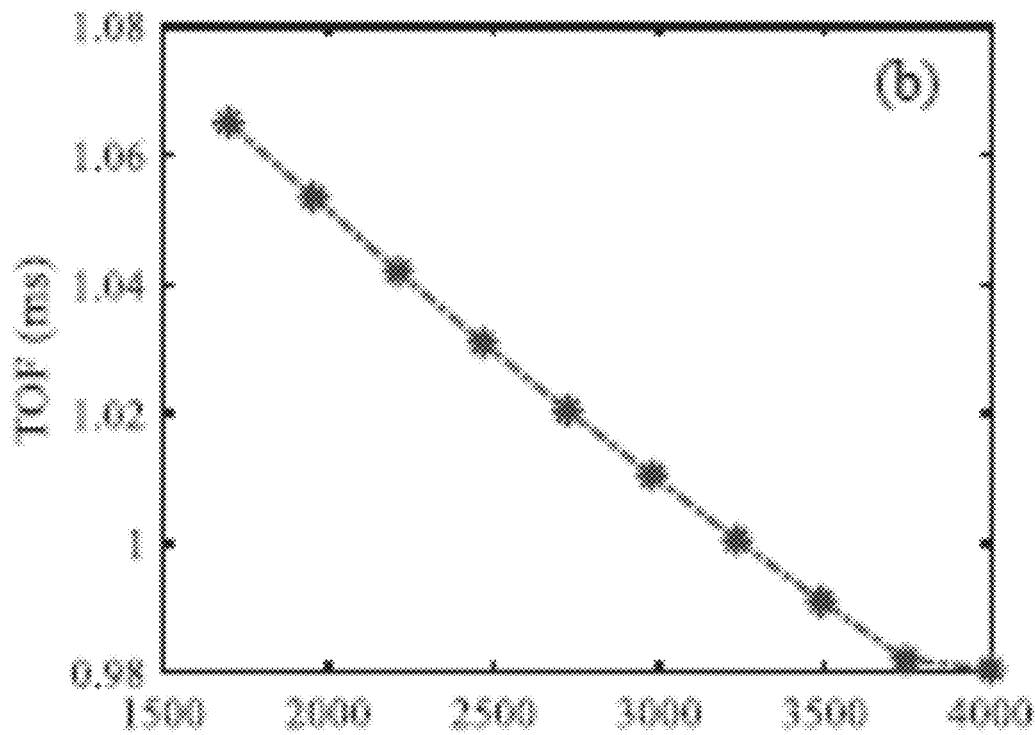
Figure 9C:
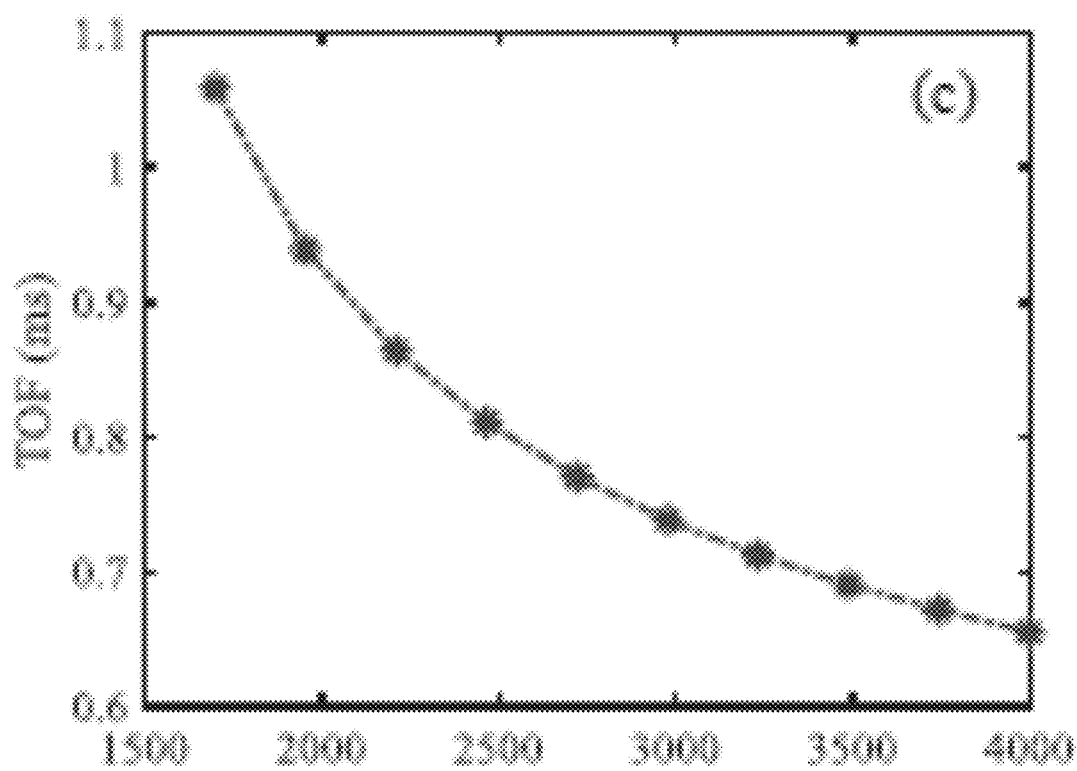
Figure 9D:
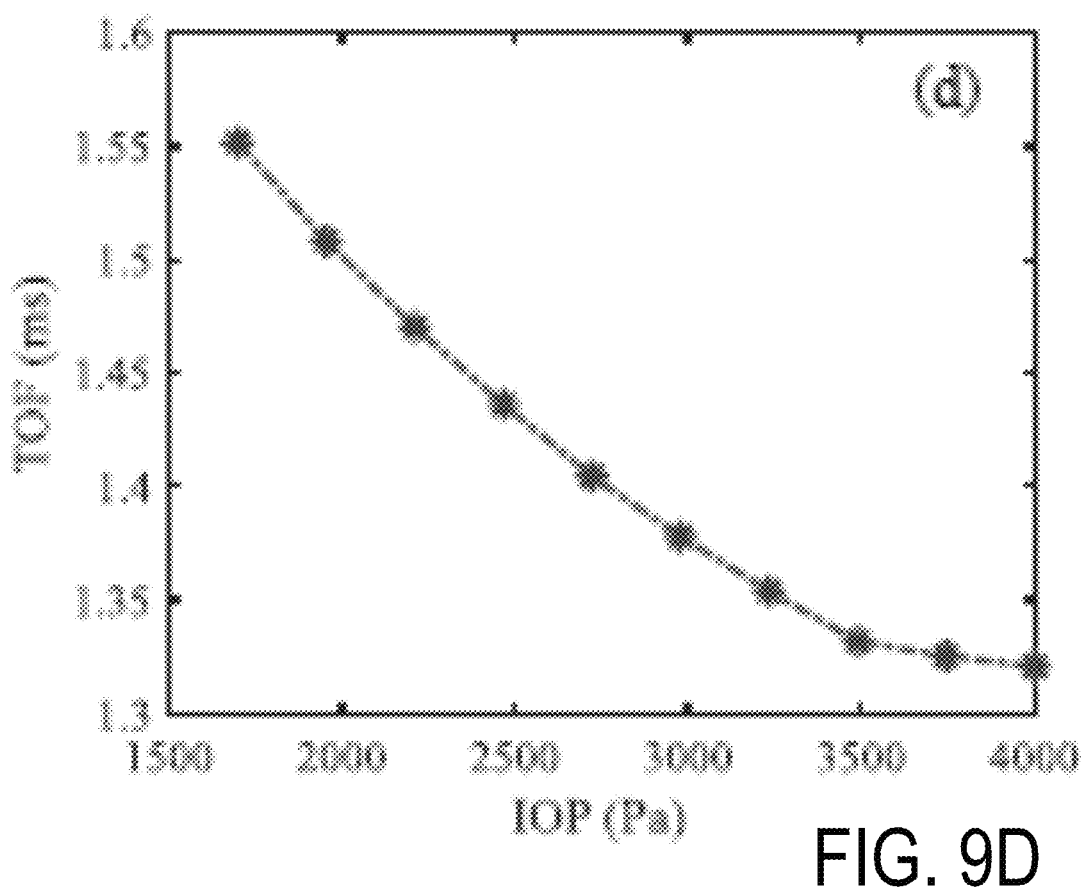

It can be understood from this equation that a lighter and softer particle has a greater contact time, and this is visible in the numerical results shown in FIGS. 7A-7D. FIG. 7D also shows that some reflected pulses consist of "twin-peaks". This phenomenon has been observed in other solitary wave applications, including the interaction of the waves with tennis balls. The twin-peaks are not generally used or required for effective IOP measurements, but in some examples they may be recorded or used to determine characteristics of the eye or instrument.

To quantify the effect of the IOP on the amplitude and time of flight of the primary reflected wave, FIGS. 8A-8D presents the amplitude of the reflected wave normalized with respect to the amplitude of the incident wave (PSW/ISW). The results associated with the four chains are presented. With one exception (FIG. 8A), each of the plots reveals a monotonic dependency of the wave feature with respect to the pressure. As can be seen from the figures, the amplitude is proportional to the eye pressure. When the pressure increases, the cornea becomes stiffer and less acoustic energy is converted into the cornea deformation leading to a stronger PSW. A rapid evaluation of the extreme pressures at 12 mmHg (1700 Pa) and 30 mmHg (4000 Pa) reveals that the normalized amplitude associated with the 2 mm PTFE chain increases by 20% across the interval.

A similar analysis was conducted for the TOF and the results are presented in FIGS. 9A-9D. Overall, this feature is inversely proportional to the pressure; as the cornea becomes softer (lower IOP), the contact time between the last bead of the chain and the cornea increases, delaying the arrival of the reflected pulses. In addition, the lower the amplitude of the reflected wave the slower is its speed, increasing further the TOF of the PSW.

Figure 10A:
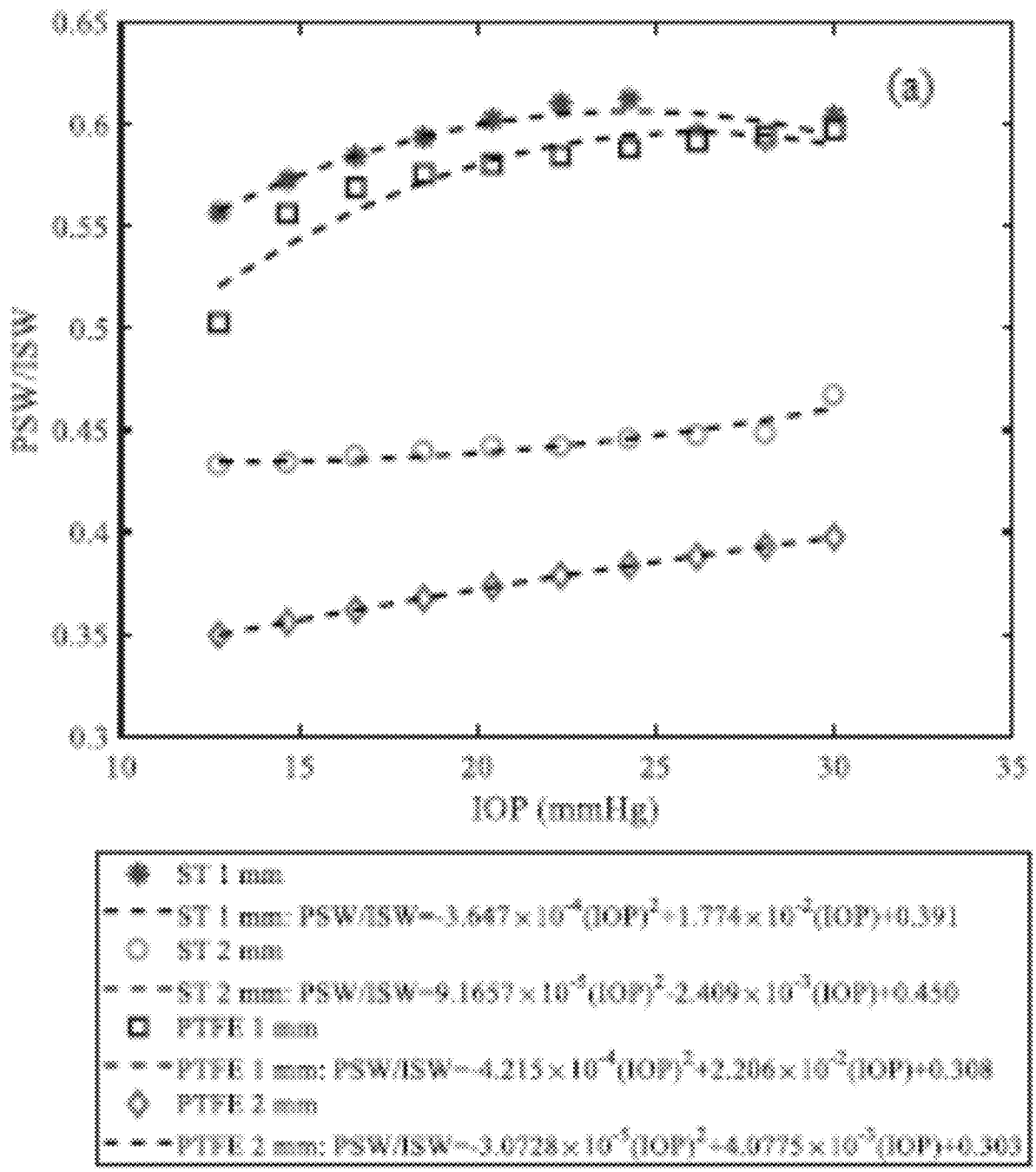
FIG. 10A is a graph of numerical values of ratio of primary reflected solitary wave (PSW) to incident solitary wave (ISW) for the 1 mm steel chain, the 2 mm steel chain, the 1 mm PTFE chain, and the 2 mm PTFE chain, for different IOPs.
Figure 10B:
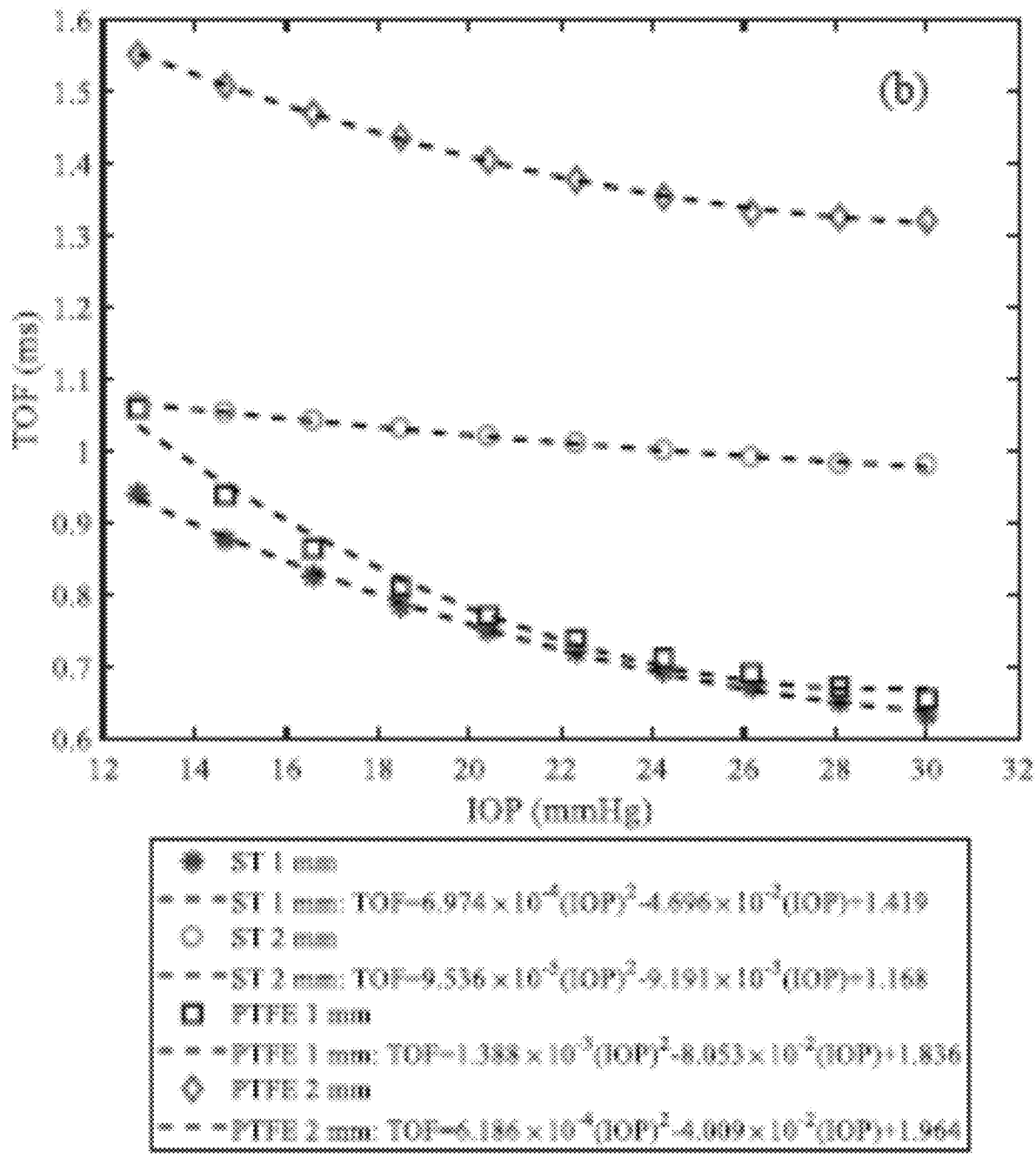
FIG. 10B is a graph of time-of-flight waveforms recorded at the center of the 10th particle of the four different 20-bead chains, for different IOPs.

To quantify the sensitivity of the proposed four chain designs with respect to the IOP variation, FIG. 10A (normalized amplitude) and FIG. 10B (time of flight) overlap the numerical results presented in FIGS. 8A-8D and FIGS. 9A-9D, respectively. The numerical data were interpolated with a second degree polynomial. The equations with the highest coefficients reveal the chain that provides the highest sensitivity to the variation of the eye pressure. The plots shown in FIGS. 10A-10B show that the chain made of twenty 1-mm diameter PTFE particles is the most sensitive to the IOP variation and therefore should be considered for the experimental validation of the proposed tonometer.

These models and experiments investigated numerically the effects of the intraocular pressure on the interaction between highly nonlinear solitary waves propagating along 1-dimensional chains of spherical particles and the cornea of young adults, in contact with one end of the chain. The study evaluated the feasibility of a solitary-wave based tonometer to measure the IOP. Engineering principle not yet explored in ophthalmology were applied to this biomedical problem by implementing a finite element formulation coupled to a discrete mass-spring model. It was found that the travel time and the amplitude of the waves reflected at the interface between the last particle of the chain and the cornea is affected by the internal pressure. These dependencies were quantified numerically by taking into account the fact that the stiffness of the cornea is a function of the pressure. Examples disclosed apparatus and methods can use these principles to effect solitary wave based tonometry measurements though disclosed examples are not necessarily limited by the disclosed models and principles.

In the models and experiments, certain characteristics were ignored or simplified, such as the effect of the eyelid, and the analysis focused on a specific value of the cornea radius and thickness. The stiffness of the cornea can be understood to be a function of the pressure, loading direction, and loading rate, as well as cornea and/or eyelid stiffness and/or thickness, and the presented model can be expanded to account for a broad range of geometric and mechanical characteristics of the eyeball, including variation of selected parameters across patient groups. In some examples, selected parameters can be accounted for in measurement estimates, such as between different patients or patient subsets (age, race, sex, medical history, etc.), or as updated through additional or refined modeling.

In a clinical setting, instrument examples can be calibrated to the physiological properties of the patient's cornea, such as eyeball diameter, eyelid thickness and/or age, and corneal thickness and modulus, and corneal radius, thickness, and modulus can be quantified to determine how physiological parameters affect solitary wave features and suitable parameter ranges for solitary-wave based tonometry applicability. In some examples, acquired patient-specific information can be used by the solitary wave-based tonometer (e.g., input by a user, inferred through solitary wave detection, or determined from other detection) to automatically or manually adjust device settings, including change solitary wave characteristics.

Example Embodiments

Figure 11:
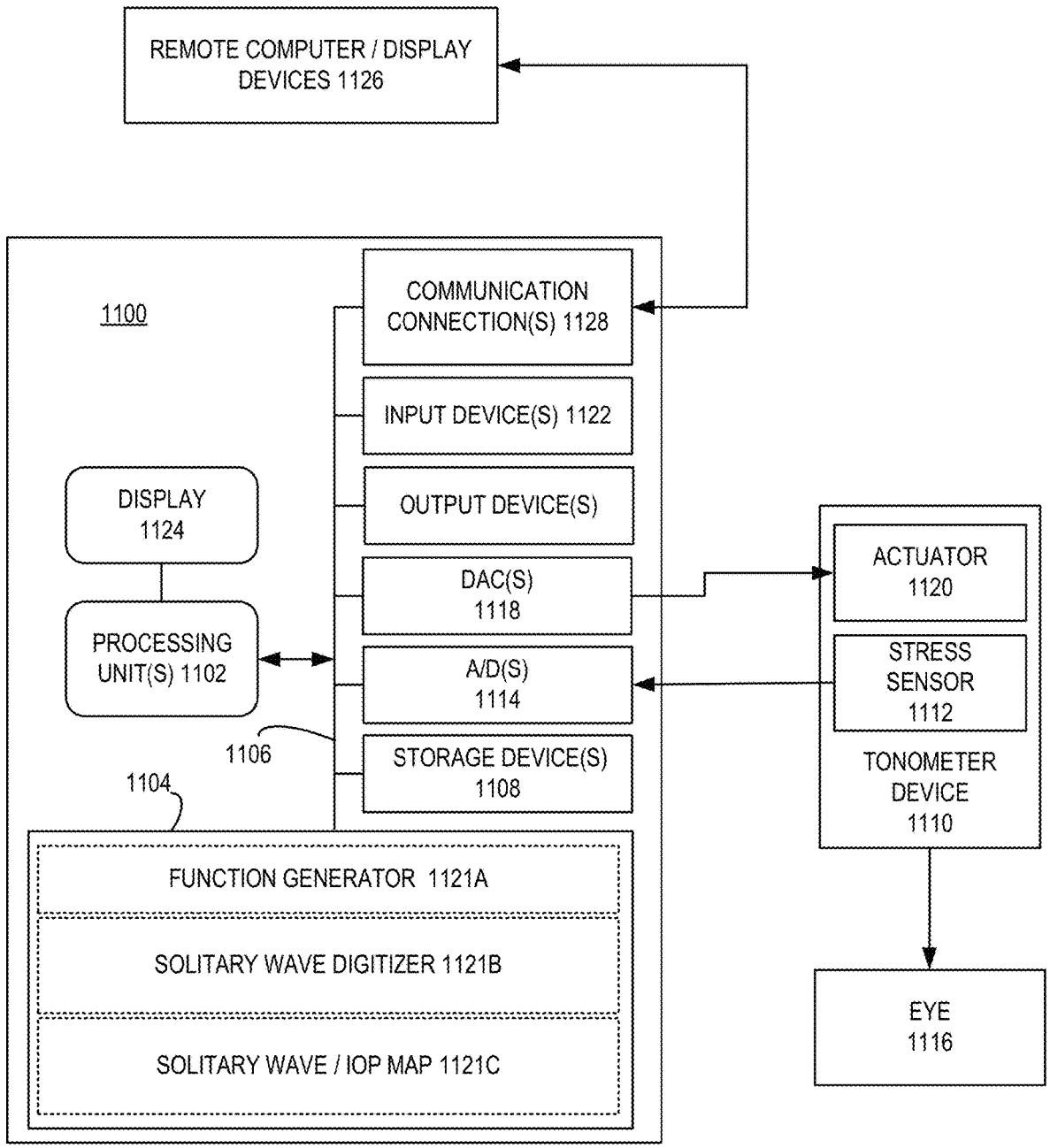
FIGS. 11-12 are schematics of tonometry systems.

FIG. 11 shows an example implementing tonometry detection on a hardware platform, such as a computing device 1100. In general, the following discussion provides a brief, general description of an exemplary computing environment in which the disclosed solitary-wave based tonometry detection and IOP estimation techniques may be implemented. Although not required, the disclosed technology is described in the general context of computer-executable instructions, such as program modules, being executed by a computing unit, dedicated processor, multiple processors, or other digital processing system or programmable logic device. Generally, program modules include routines, programs, objects, components, data structures, etc., that perform particular tasks or implement particular abstract data types. Moreover, the disclosed technology may be implemented with other computer system configurations, including hand-held or mobile devices, personal computers (PCs), multiprocessor systems, microprocessor-based or programmable consumer electronics, network PCs, minicomputers, mainframe computers, dedicated processors, MCUs, PLCs, ASICs, FPGAs, CPLDs, systems on a chip, and the like. The disclosed technology may also be practiced in distributed computing environments where tasks are performed by remote processing devices that are linked through a communications network. In a distributed computing environment, program modules may be located in both local and remote memory storage devices. For example, processing (including function generation, waveform digitization, or both) can be distributed between local and remote devices. In some examples, intensive processing can be dedicated to remote computers or mobile devices.

With reference to FIG. 11, an exemplary system for implementing the disclosed technology includes the computing device 1100 that includes one or more processing units 1102, a memory 1104, and a system bus 1106 coupling various system components, including the system memory 1104, to the one or more processing units 1102. The system bus 1106 may be any of several types of bus structures including a memory bus or memory controller, a peripheral bus, and a local bus using any of a variety of bus architectures. The memory 1104 can include various types, including volatile memory (e.g., registers, cache, RAM), non-volatile memory (e.g., ROM, EEPROM, flash memory, etc.), or a combination of volatile and non-volatile memory. The memory 1104 is generally accessible by the processing unit 1102 and can store software in the form computer-executable instructions that can be executed by the one or more processing units 1102 coupled to the memory 804. In some examples, processing units can be configured based on RISC or CISC architectures, and can include one or more general purpose central processing units, application specific integrated circuits, graphics or co-processing units or other processors. In some examples, multiple core groupings of computing components can be distributed among system modules, and various modules of software can be implemented separately.

The computing device 1100 can further include one or more storage devices 1108 such as a hard disk drive, flash drive, etc., which can be connected to the system bus 1106 by a storage communications interface. The drives and their associated computer-readable media provide nonvolatile storage of computer-readable instructions, data structures, program modules, and other data for the computing device 1100. Other types of non-transitory computer-readable media which can store data that is accessible by a computing device may also be used in the exemplary computing environment. The storage 1108 can be removable or non-removable and can be used to store information in a non-transitory way and which can be accessed within the computing environment.

The computing device 1100 can be coupled through one or more analog to digital convertors (A/Ds) 1114 to a stress wave sensor 1112 housed in the computing device 1100 (forming a tonometer unit) or in a separate tonometer device 1110. Thus, in some examples, the computing device 1100 (or selected parts of the computing device 1100) can be integrated into a tonometer unit that can couple to an eye 1116. In some examples, the computing device 1100 with stress wave sensor 1112 can comprise application specific hardware/software, such as the tonometer unit, specifically configured for detection of solitary waves and estimation of intraocular pressure based on characteristics of the detected solitary waves. During operation, the stress wave detector 1112 detects a primary and/or secondary reflected solitary wave signal after an incident solitary wave propagates along a chain of particles and is reflected by the eye 1116, and sends the detected reflected solitary wave signal to the computing device 1100 for signal analysis and production of an IOP estimate for the eye 1116. The computing device 1100 can include digital to analog converters (DACs) 1118 coupled to the bus 1106, e.g., for control of external analog devices, such as an actuator 1120 used to produce the incident solitary wave that propagates along the chain.

The software, e.g., stored in the memory 1104 at 1121A, can automate the measurement of IOP for a user by generating a solitary waveform suitable for application with an actuator (such as an electromagnet, transducer, etc.) to a chain of particles configured to propagate a nonlinear incident solitary wave to an eyelid. In further examples, the function generation can be performed in hardware and/or in a device separate from the computing device 1100. Example functions to be generated can include square waves, sinusoidal waves, simple pulses, variable pulses, etc. The memory at 1121B can further include a solitary wave digitizer that can be used to digitize the detected reflected solitary wave signal. In further examples, the waveform digitization can be performed in hardware and/or in a device separate from the computing device 1100. The memory at 1121C can include a mapping between solitary wave characteristics and IOP (e.g., with a look-up table) to produce an estimate of an IOP of the eye 1116 by comparing characteristics of the digitized waveform, such as a monotonic dependence between IOP and amplitude and time-of-flight (ToF) of one or more of the reflected solitary waves (including primary and secondary waves or multiple wave samples) or other waveform characteristics, such as amplitudes of incident, primary, and/or secondary solitary waves, time of flight of primary and/or secondary solitary waves, a width at half amplitude of each of the three waves, and any declination in terms of their ratios or product, such as the ratio of the amplitude of the PSW to the amplitude of the ISW or the product of the two amplitudes.

In addition to the above, a number of program modules (or data) may be stored in the storage devices 1108 including an operating system, one or more application programs, other program modules, and program data. A user may enter commands and information into the computing device 1100 through one or more input devices 1122 such as a keyboard, a pointing device such as a mouse, or control buttons to initiate or control a tonometry test or to display an IOP estimate. Other input devices may include a digital camera, microphone, satellite dish, scanner, display, or the like. These and other input devices are often connected to the one or more processing units 1102 through a serial port interface that is coupled to the system bus 1106, but may be connected by other interfaces such as a parallel port or universal serial bus (USB), or integrated wiring. A display 1124 such as an LCD display, monitor, or other type of display device can also be connected to the system bus 1106 via an interface, such as a video adapter. Some or all data and instructions can be communicated with a remote computer 1126 through communication connections 1128 (e.g., wired, wireless, etc.) if desired. In some examples, the remote devices 1126 can include one or more mobile devices or other computing devices that can be used to provide the majority of signal generation, processing, and/or IOP estimation, preferably with the computing device 1100 having pared down functionality sufficient to provide integration of the computing device 1100 with the stress sensor 1112 as a tonometer unit so that the tonometer unit can be hand-held by a user to self-administer the tonometer device to the user's eye. In some examples where the stress sensor 1112 is part of the tonometer device 1110 and separate from the computing device 1100, the computing device 1100 can be a mobile device, such as a smartphone or hand-held computing unit.

Figure 12:
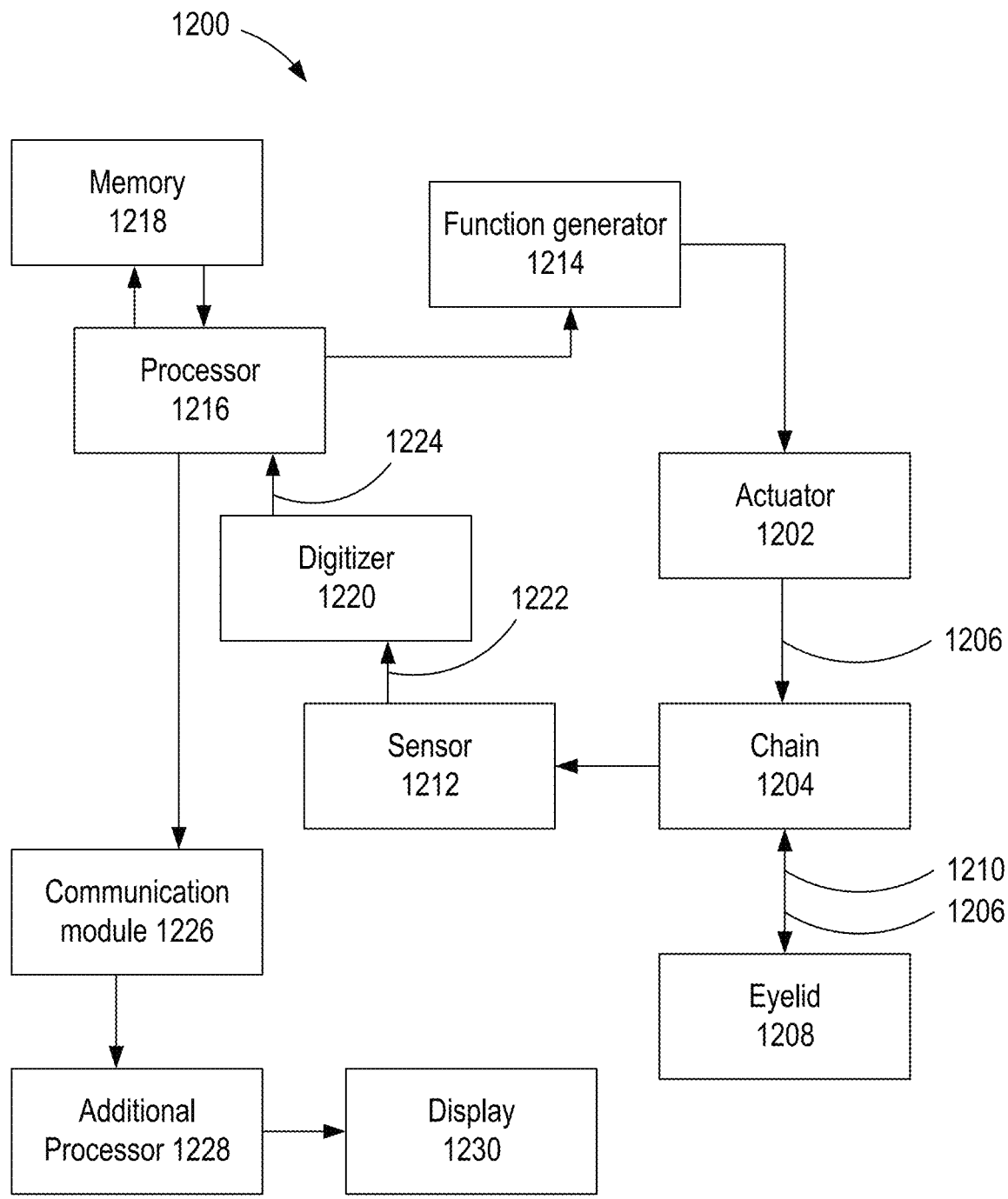

FIG. 12 shows an example system 1200 that can be used to detect intraocular pressure of an eye. The system 1200 includes an actuator 1202, such as a mechanical, electrical, or electro-mechanical actuator coupled to a chain 1204 of particles suitable to propagate a solitary wave 1206. The actuator 1202 is typically configured to strike, impact, vibrate, or otherwise induce the solitary wave 1206 to propagate along the chain 1204. The chain 1204 is typically supported in a housing (not shown) that can support the chain 1204. The housing can be used to house additional components (and related interconnections) of the system 1200 in various examples, such as the actuator 1202. The chain 1204 in the housing is removably coupled to an eyelid 1208 of a patient having an IOP to be measured, such as through a membrane, arcuate or circular ridge, detent, or other support that allows transmission of the solitary wave 1206 to the eyelid 1208 so that one or more reflected waves 1210 can be received by the chain 1204 from the eyelid 1208. The system 1200 further includes a sensor 1212 coupled to the chain 1204 and that is configured to detect characteristics of the one or more reflected waves 1210 propagating back through the chain 1204 from the eyelid 1208. Various examples of the sensor 1212 can include piezoelectric sensors, magnetic coils, or any other sensor suitable for detection stress waves.

In representative examples, the system 1200 further includes a function generator 1214 configured to generate selected solitary wave waveforms that can be directed to the actuator 1202. The function generator 1214 is typically coupled to a processor 1216 configured with processor-executable instructions stored in a memory 1218 that can select and control the characteristics of the solitary wave waveforms generated by the function generator 1214 and the solitary wave 1206 produced with the actuator 1202. Example waveforms can vary in complexity, with some examples having arbitrary shapes, others having simple on states and off states, etc. In some examples, the incident solitary wave may be induced by a mechanical or electrical device that enables the mechanical impact of the striker onto the chain. In some examples, a digitizer 1220 is coupled to the sensor 1212 so as to receive a reflected solitary wave signal 1222 from the sensor 1212, to then produce a digitized waveform 1224 from the reflected solitary wave signal 1222 and provide the digitized waveform 1224 to the processor 1216 (or another processing unit). In some examples, the processor 1216 is configured to determine the IOP of the eye based on the digitized waveform 1224 by comparing a time difference between generation of the solitary wave 1206 (or a suitable offset) and detection of the reflected solitary wave 1210. In further examples, a communication module 1226 can receive and then transmit the digitized waveform 1224 or related detected reflected solitary wave data wirelessly or through a wired communication line to an additional processor 1228 or computing unit. In some examples, the additional processor 1228 can be configured to provide additional computation or processing of the digitized waveform 1224 or related detected reflected solitary wave data, such as intensive signal processing, so that the other components (such as the processor 1216) can be smaller and more streamlined (e.g., with a smaller form factor and reduced power requirements) for use in a portable solitary-wave based tonometer. In further examples, the function generator 1214 and/or digitizer 1220 can be coupled to the processor 1216 through the communication module 1226 instead of between the processor 1216 and actuator 1202 or the processor and sensor 1212, respectively. In a particular example, the communication module 1226 communicates wirelessly to a handheld or mobile device (such as a smartphone) that includes one or more applications ("apps") configured to provide signal processing or solitary-wave based IOP calculations and estimates. In representative examples, the system includes a display 1230 that can show IOP estimates to a user of the device. As shown, the display 1230 is coupled to the additional processor 1228 but the display 1230 can also be coupled to the processor 1216, and can be situated locally, such as on the housing that houses the chain 1204, or elsewhere in relation to components of the system 1200.

Figure 13:
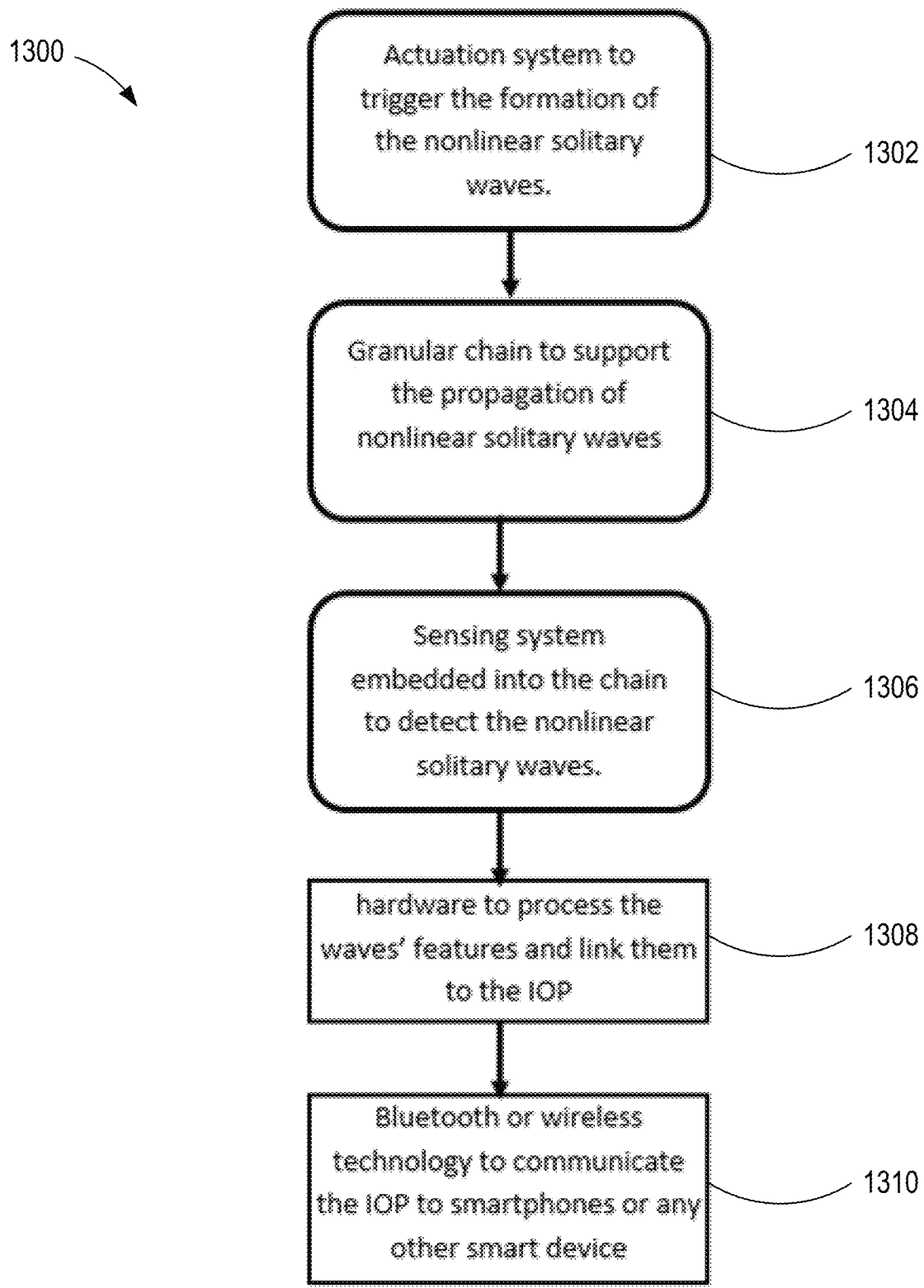
FIG. 13 is a flowchart of a tonometry system arrangement.

FIG. 13 shows an example tonometry system arrangement 1300 that includes, at 1302, an actuation system configured to trigger the formation of a nonlinear solitary wave, and at 1304, a granular chain coupled to the actuation system and configured to support the propagation of nonlinear solitary waves. The tonometry system arrangement 1300 further includes, at 1306, a sensing system coupled to (e.g., embedded into) the chain to detect nonlinear solitary waves propagating through the chain including reflected solitary waves, and at 1308, hardware coupled to the sensing system and configured to receive a signal associated with the detected nonlinear solitary wave to process the wave's features and to associate or link the features to an IOP of an eye coupled to the granular chain. The tonometry system arrangement 1300 can also include Bluetooth or other wireless (or wired) communication modules that communicate the IOP measurement to one or more mobile devices, such as a smartphone or other smart device.

Figure 14:
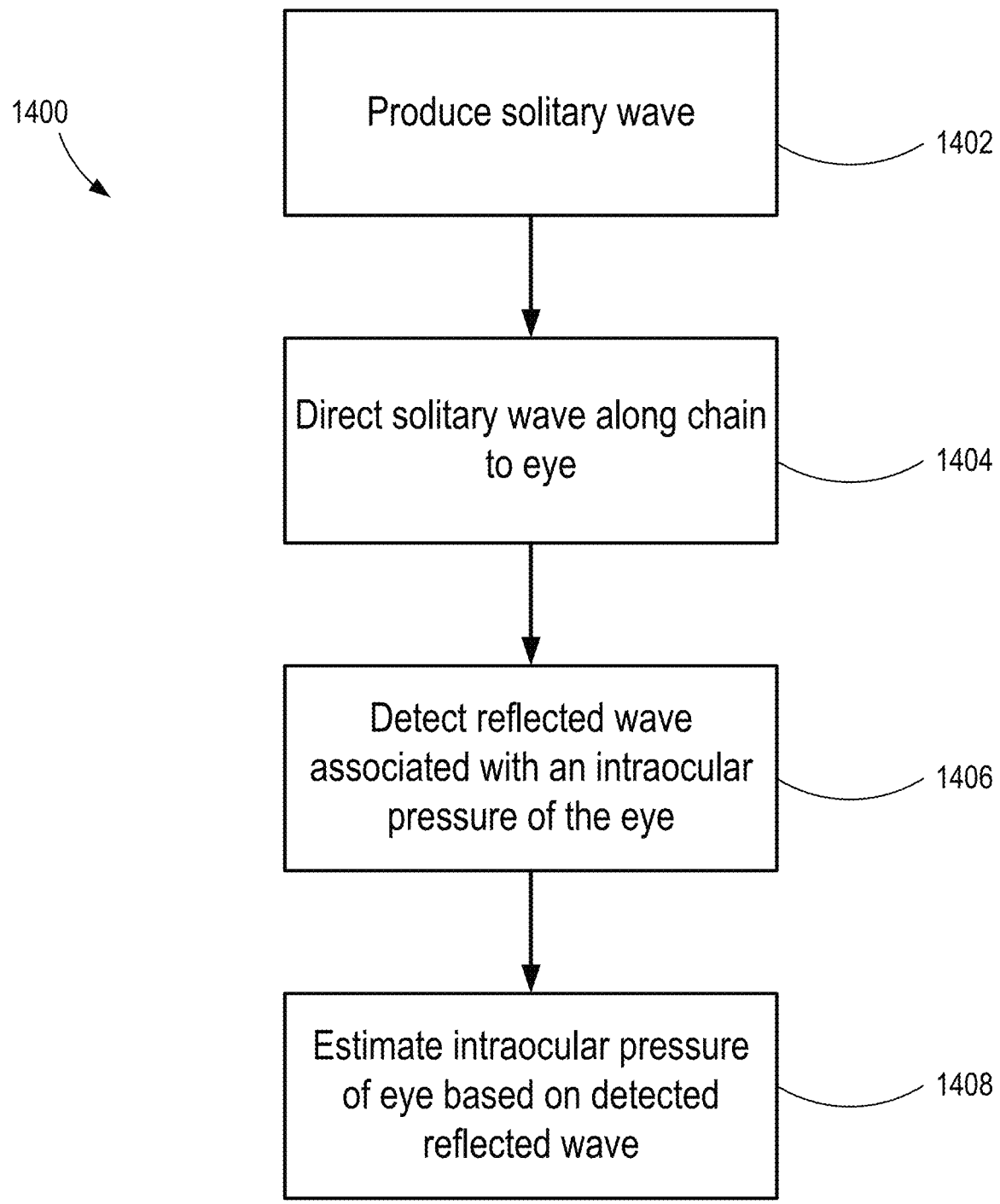
FIG. 14 is a flowchart of an example tonometry method.

FIG. 14 is an example tonometry method 1400 that includes, at 1402, producing a solitary wave, such as with an actuator. The actuator can be coupled to solitary wave chain so that, at 1404, the produced solitary wave can be directed along the chain to an eye of a patient as an incident solitary wave. In representative examples, the chain is coupled to an eyelid of the patient so that tonometry can be performed without contacting the sclera or performing an invasive procedure on the eye. The incident solitary wave reaches the eye and forms a reflected solitary wave that propagates back along the chain so that at 1406, the reflected wave can be detected. From a comparison of various characteristics of the detected reflected solitary wave in relation to characteristics of the incident solitary wave (such as time of flight, amplitude, etc.), at 1408, an estimate of an IOP of the eye can be made.

Figure 15:
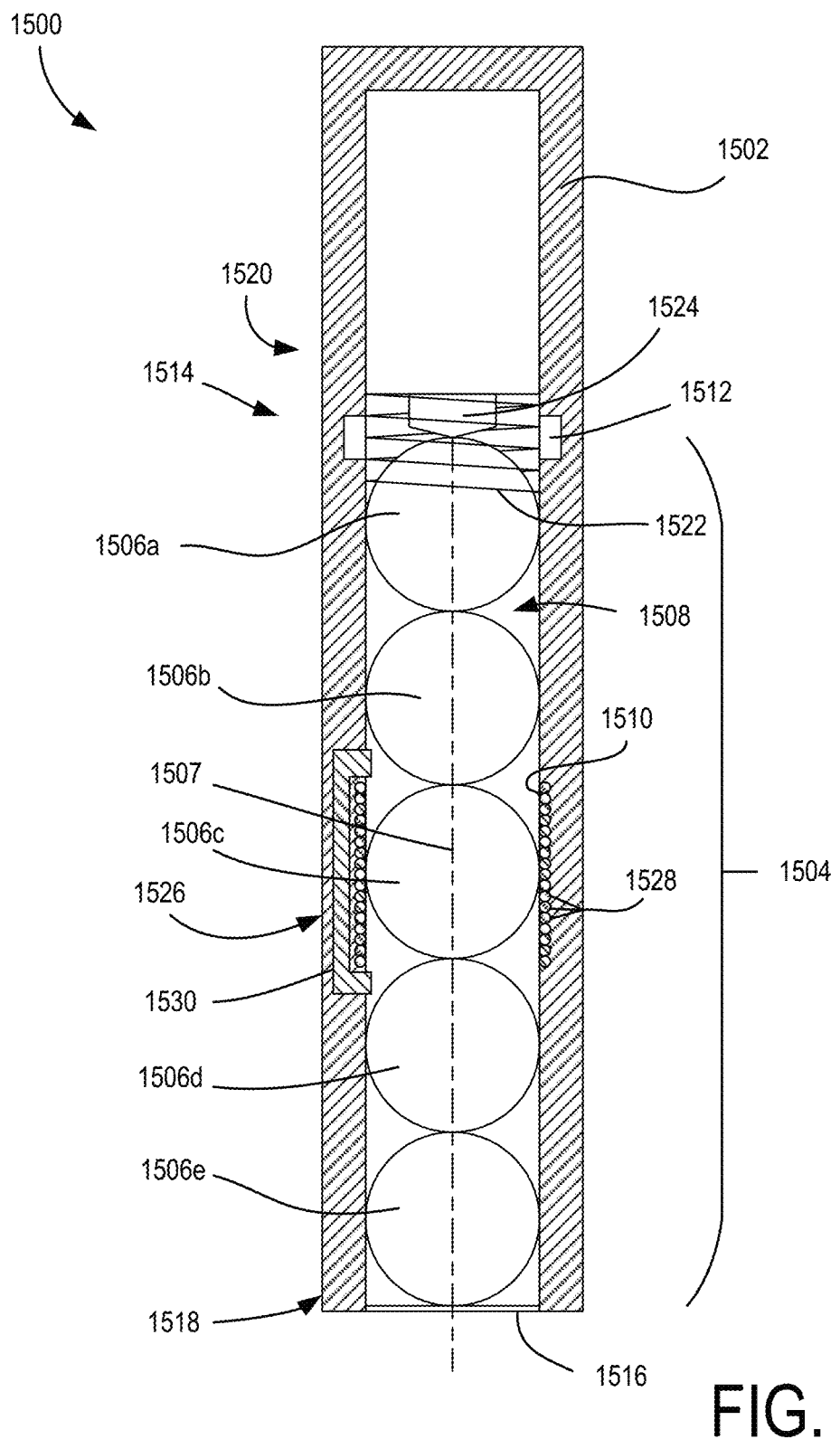
FIG. 15 is a side partial cross-sectional view of a tonometry device.

An example tonometry device 1500 is shown in FIG. 15. The tonometry device 1500 includes a housing 1502 shown in cross-section to reveal various components including internally housed components. For example, a chain 1504 of a plurality of loosely coupled particles 1506a-1506e (or "grains") are situated along an axis 1507 in a longitudinal interior volume 1508 defined by an interior surface 1510 of the housing 1502. In representative examples (including as shown), the particles 1506a-1506e are spherical in shape. Other shapes can be used as well provided they support the propagation of nonlinear solitary waves. In selected examples, particles are cylindrical, elliptical, concave, or convex, and provide curved contact surface engagement between adjacent particles. As shown, the axis 1507 is linear, but curved, bent, forked, or other axial shapes can be provided. In various examples, the number of particles can be selected in the range of between about five and about fifty. In spherical, rectangular, and elliptical particle examples, the diameter (for spherical) or minor axis (for elliptical and rectangular) can be selected in the range of about 100 µm to 30 mm and the Young's modulus of the material forming each particle can vary from about 0.01 GPa to about 300 GPa.

The interior surface 1510 can provide a frame or support for holding the particles 1506a-1056e. The particles 1506a-1506e are loosely coupled so that the chain 1506 can partially displace along the axis 1507 after a force is received from an actuator 1512 at a first end 1514 of the chain 1506. The actuator 1512 can be of any type suitable to produce a solitary stress wave along the chain 1506, such as an electromagnet, plunger, striker, etc. A flexible member 1516, such as a thin membrane, is situated at an opposite end 1518 of the chain 1506 and secured to the housing 1502 (e.g., with glue) to prevent particles 1506a-1506e from exiting the interior volume 1508 or significant displacement of the chain 1506. Suitable examples of the flexible member 1516 can include aluminum or elastomer sheeting. In representative examples, the flexible member 1516 as attached to the tonometry device 1500 can be brought into direct contact with an eyelid for a tonometry measurement. In some examples, a compressive member 1520 such as a spring 1522 and/or magnet 1524 can be situated at the first end 1514, the opposite end 1518, or other locations in the housing 1502 to provide a suitable compression force between the particles 1506a-1506e. Other suitable compressive members can include flexible o-rings, collars, wadding material, latches, etc.

The tonometry device 1500 can further include a stress wave detector 1526 coupled to or forming a part of at least one of the particles 1506a-1506e of the chain 1502. As shown, the stress wave detector 1526 includes a coil 1528 (shown in cross-section) encircling particle 1506c and a permanent magnet 1530 (shown in cross-section) that applies a magnetic bias across the coil 1528 in the direction of the axis 1507. In other examples, the stress wave detector 1526 can include a piezo-mechanical system. As an incident solitary wave propagates along the chain 1506 towards the opposite end 1518 and passed the stress wave detector 1526 or as a reflected solitary wave propagates along the chain 1506 towards the first end 1514 and passed the stress wave detector 1526, electrical signals are produced in the coil 1528 that can be sent to additional components 1526, such as an analog-to-digital converter, waveform digitizer, and/or computing unit. The electrical signals can correspond to stress wave detection events and the signals can be converted into IOP measurement estimates. By way of example, the additional components 1526 can also include programmable measurement hardware, batteries, wireless communication modules, plugs, access ports, or other components, situated in the housing 1502. During operation the additional components 1526 can be used to produce the estimates of IOP. In selected examples, the IOP estimates can be sent, or IOP computation or other signal processing can be sent, via wireless communication (e.g., WiFi, Bluetooth, NIR, etc.) to a mobile device or other external computing device.

Figure 16:
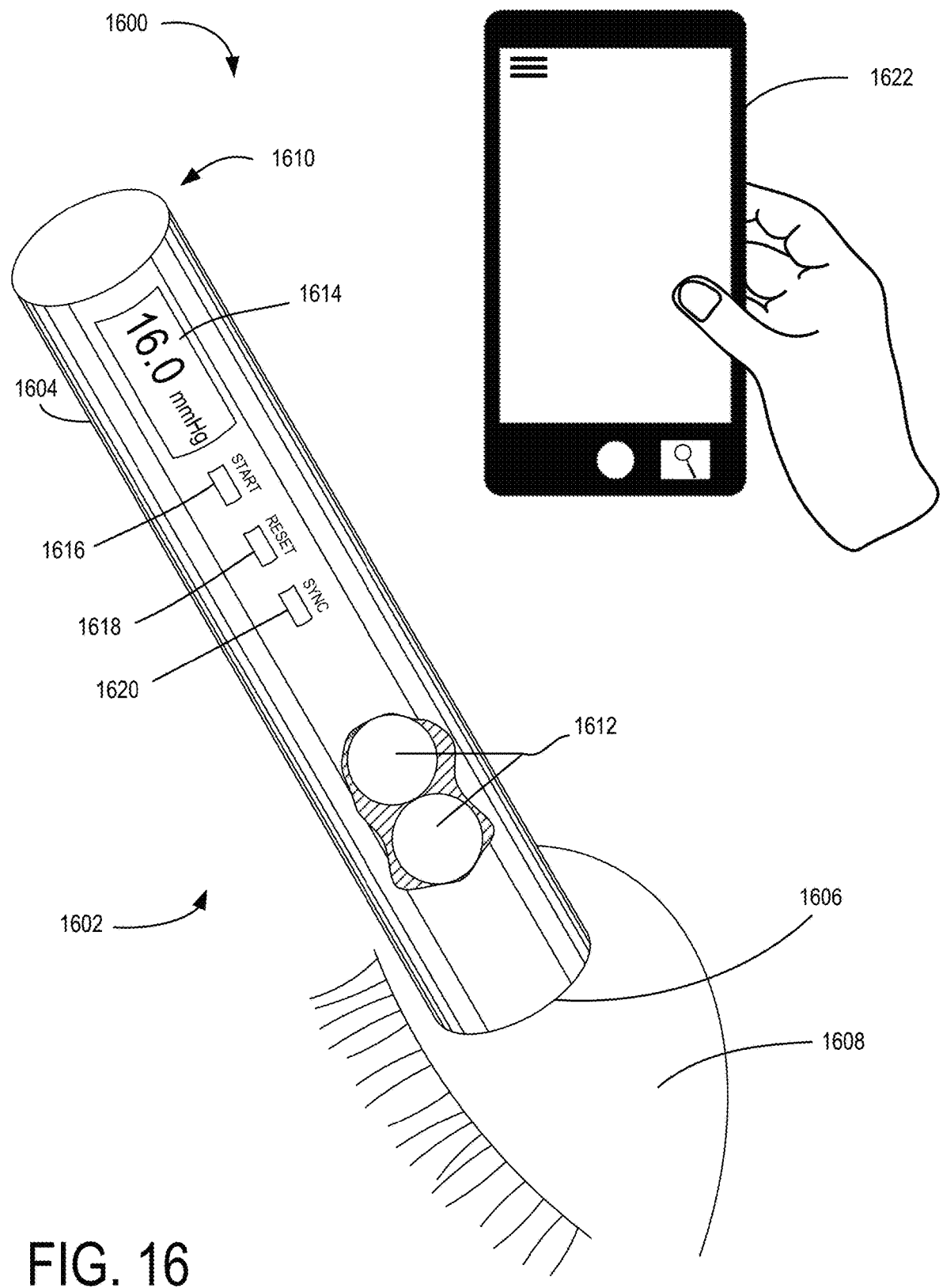
FIG. 16 is a perspective view of a tonometry system being applied to a user's eye.

FIG. 16 shows an example tonometry system 1600 that includes a tonometer device 1602. In representative examples, the tonometer device 1602 includes a body 1604 having a cylindrical shape and a form factor similar to a pen. The body 1604 includes an application end 1606 that can be applied to an eyelid 1608 of a user and an opposite end 1610 housing various electronic circuitry. In some examples, the body 1604 has a shape that can be gripped by a user, such as at the opposite end 1610, so that the user can apply the application end 1606 to the user's eyelid to self-administer a tonometry test to produce an IOP estimate. During operation, a nonlinear incident solitary wave is produced within the tonometer device 1602 and directed along a particle chain 1612 (shown in cut-away) to the eyelid 1608, and a reflected solitary wave is detected with the tonometer device 1602 at a position along the chain 1612. A display 1614 can situated on the body 1604 for showing the results of a tonometry test, such as by displaying an IOP estimate. One or more buttons or other interfaces, such as buttons 1616, 1618, 1620, can be situated on the body 1604 for providing various functions. For example, the button 1616 labeled "START" can be used to wake-up the tonometer device 1602 from a rest state and/or initiate a tonometry test, the button 1618 labeled "RESET" can be used to reset the tonometer device 1602 before initiation of another tonometry test, and the button 1620 labeled "SYNC" can be used to initiate communication link between the tonometer device 1602 and an external device, such as a mobile device 1622. In further examples, functionalities of different buttons can be combined or additional functions can be provided. In some examples, the body 1604 does not include any buttons or interfaces. In some examples, the mobile device 1622 or other external computing unit can be used to initiate and control the tonometry test.

Figure 17:
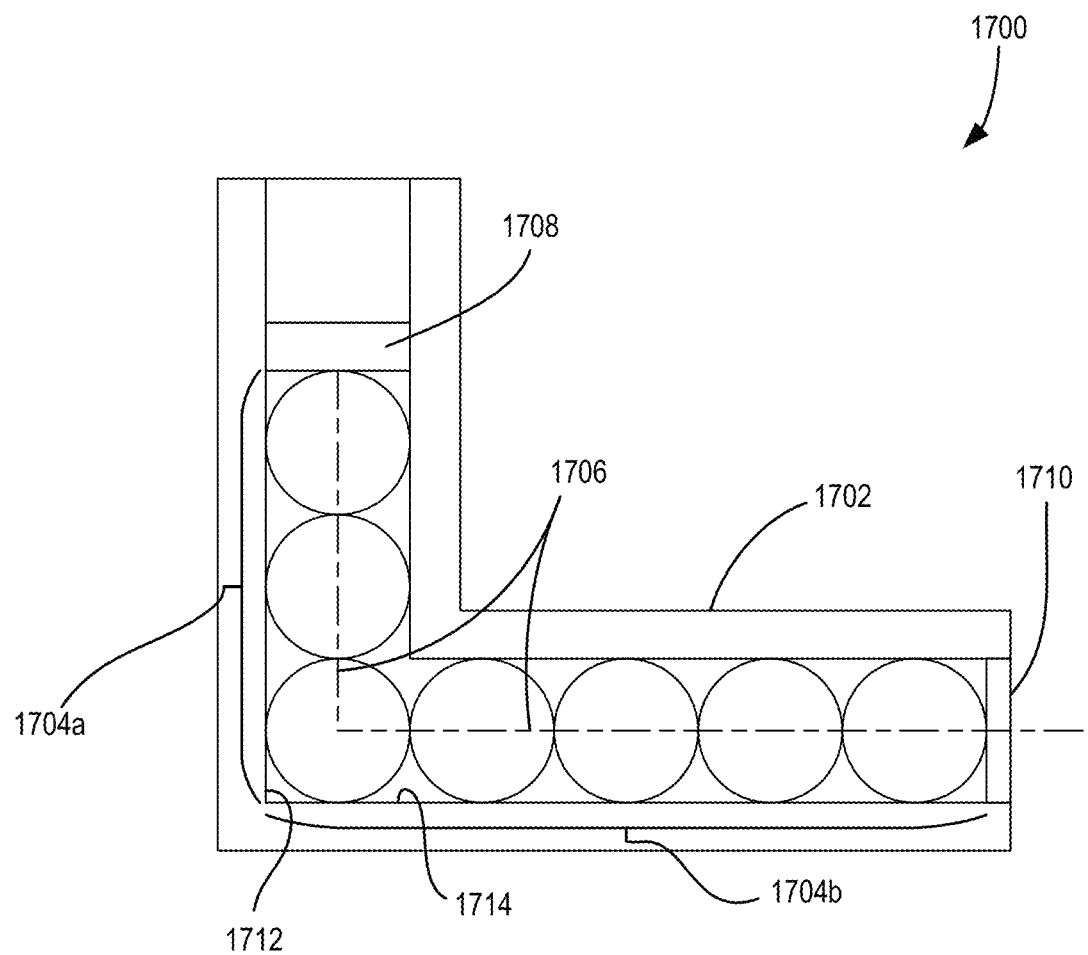
FIGS. 17-18 are side-view schematics of tonometry devices in bent configurations.

FIG. 17 shows an example tonometer device 1700 that includes a housing 1702 that supports a particle chain, including a first leg 1704a and a second leg 1704b, along a bent path 1706. During operation, an actuator 1708 produces a nonlinear solitary stress wave that propagates along the bent path 1706 towards an output surface 1710 which can be a flexible member that can be coupled to the eyelid of a person. The second leg 1704b of the particle chain can be secured in compression in the horizontal direction in FIG. 17 between a portion 1712 of an inner surface of the housing 1702 and the output surface 1710. With the tonometer device 1700 positioned for measurement such that the first leg 1704a is oriented at least in part with respect to Earth's gravity, the first leg 1704a of the particle chain can be secured in compression in the vertical direction in FIG. 17 with another portion 1714 of the inner surface of the housing 1702 and a weight of the particles of the particle chain of the first leg 1704a. Additionally or alternatively, a spring, magnet, or other compressive member can be situated in the housing 1702 to compress the first leg 1704a along the direction of the particle chain.

Figure 18:
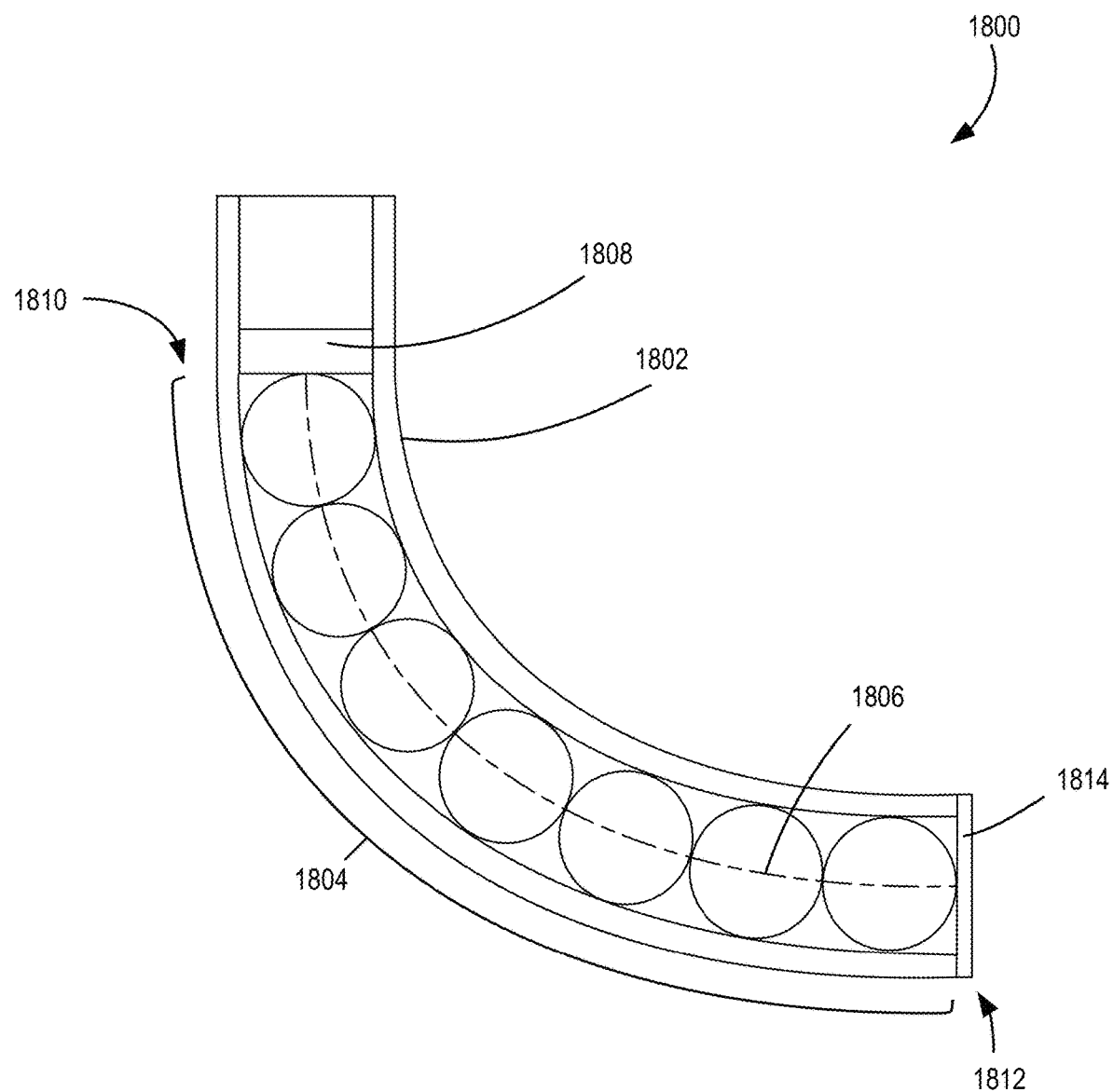

FIG. 18 shows an example tonometer device 1800 similar in some respect to the tonometer device 1700. The tonometer device 1800 includes a housing 1802 that supports a particle chain 1804 that is arranged along a bent path 1806 having a curved shape. An actuator 1808 is coupled to a first end 1810 of the particle chain 1804 and directs a nonlinear solitary wave along the particle chain 1804 to a second end 1812. A flexible member 1814 can be secured to the housing 1802 at the second end 1812 of the particle chain 1804 so that the nonlinear solitary wave can become incident on an eyelid through the flexible member 1814 for a tonometry measurement. In representative examples, the curved shape of the bent path 1806 can improve force transfer along the particle chain 1804 as compared to other shapes, such as the bent path 1706. In some examples, with the tonometer device 1800 positioned by a user such that the first end 1810 of the particle chain 1804 is oriented at least in part with respect to Earth's gravity, a weight of the particle chain 1804 can be sufficient to provide a compressive force for the particle chain 1804 during tonometry measurement.

Figure 19:
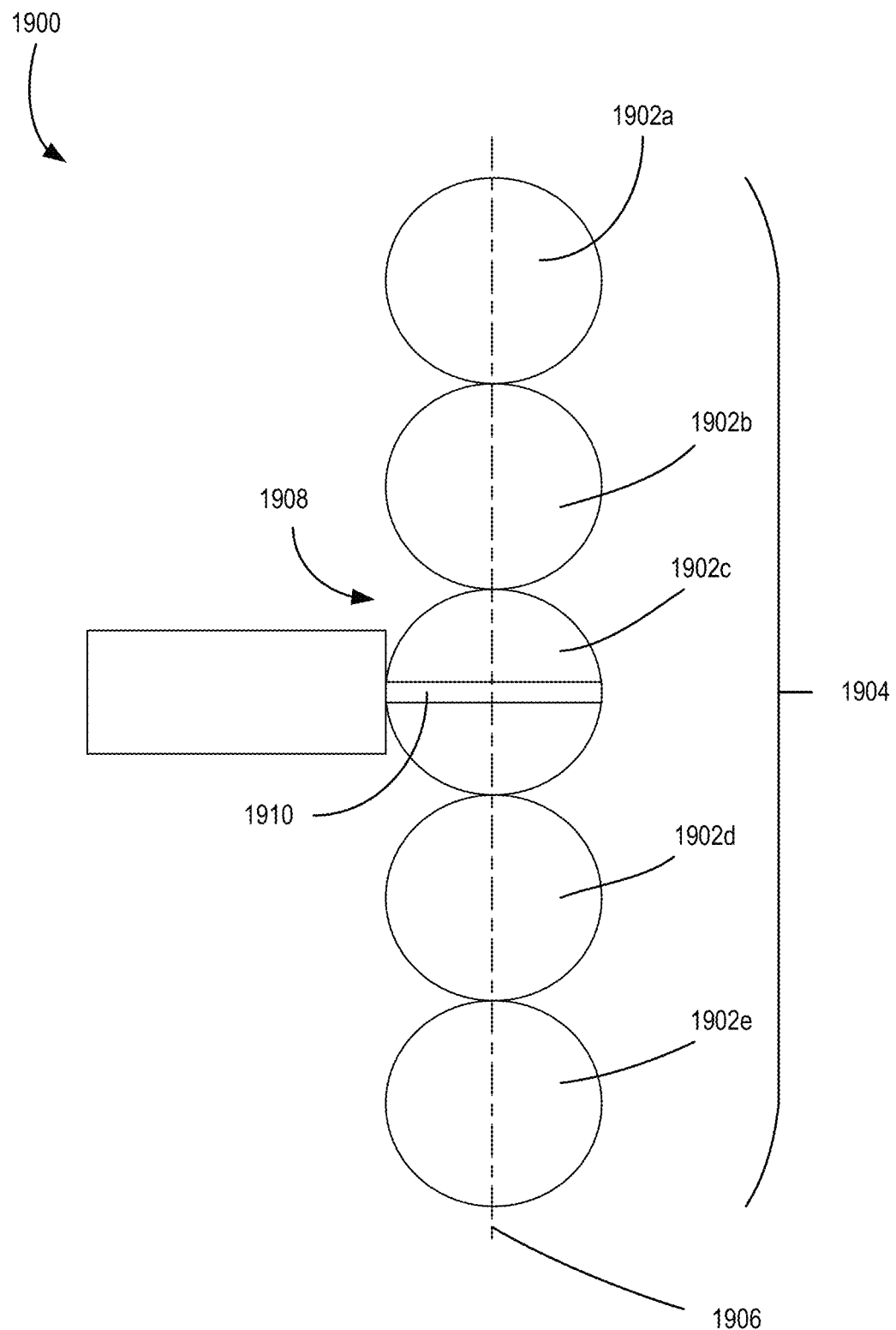
FIGS. 19-20 are side schematics of tonometry chains with a piezo-electric sensors.
Figure 20:
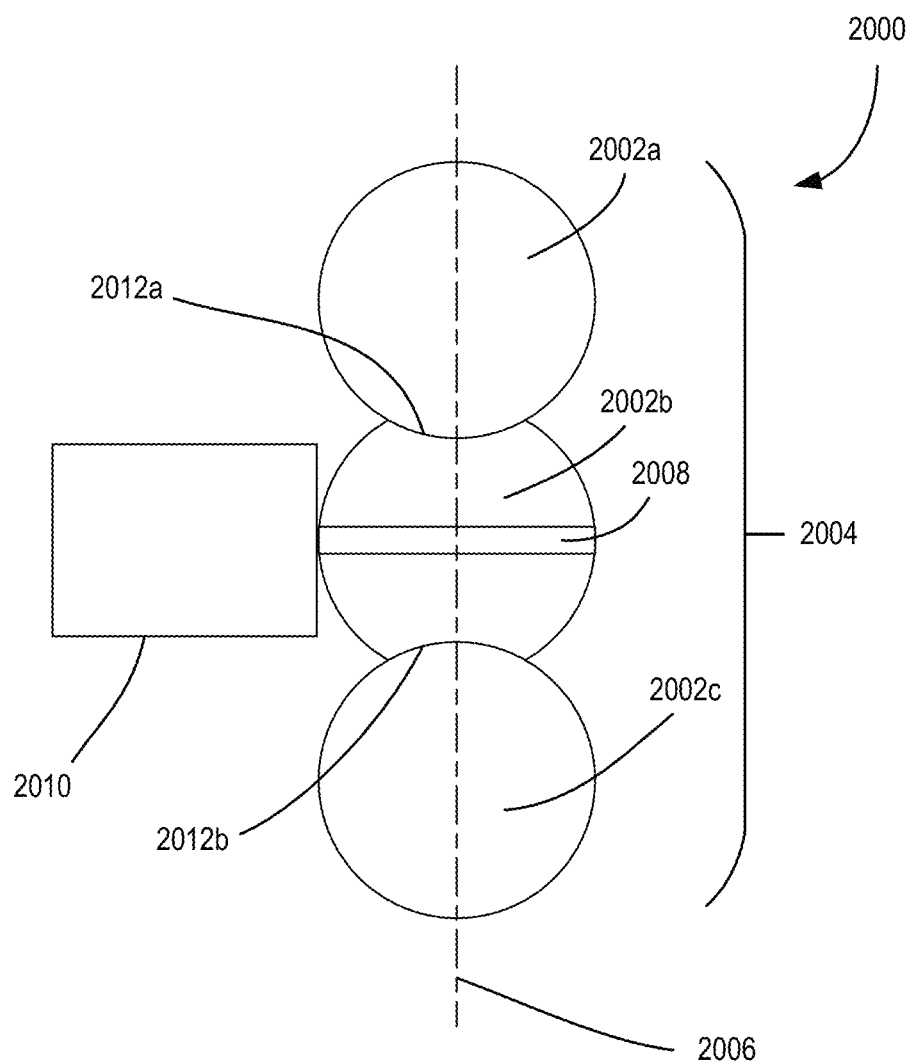

FIG. 19 shows a tonometer chain arrangement 1900 including spherical particles 1902a-1902e adjacently arranged in a loosely coupled particle chain 1904. The chain 1904 is configured to propagate solitary waves in either direction (e.g., corresponding to incident and reflected solitary waves) along a chain axis 1906. A piezo-electric sensor 1908 is coupled to the chain 1904 and includes a piezo-element 1910 formed into the particle 1902c and situated horizontally with respect to the chain axis 1906 and directions of the propagating solitary waves. FIG. 20 shows another tonometer chain arrangement 2000 similar to the tonometer chain arrangement 1900. The tonometer chain arrangement 2000 includes particles 2002a-2002c arranged in a chain 2004 along a chain axis 2006, with the particle 2002b configured with a piezo-element 2008 coupled to a piezo-electric stress wave sensor 2010. The particle 2002b includes concave surfaces 2012a, 2012b, such as dimples or other supports, configured to receive the curved spherical surfaces of the respective particles 2002a, 2002c so that the perpendicular relationship between the piezo-element 2008 and the chain axis 2006 is maintained during operation in a tonometry device.

Additional Examples

Figure 21:
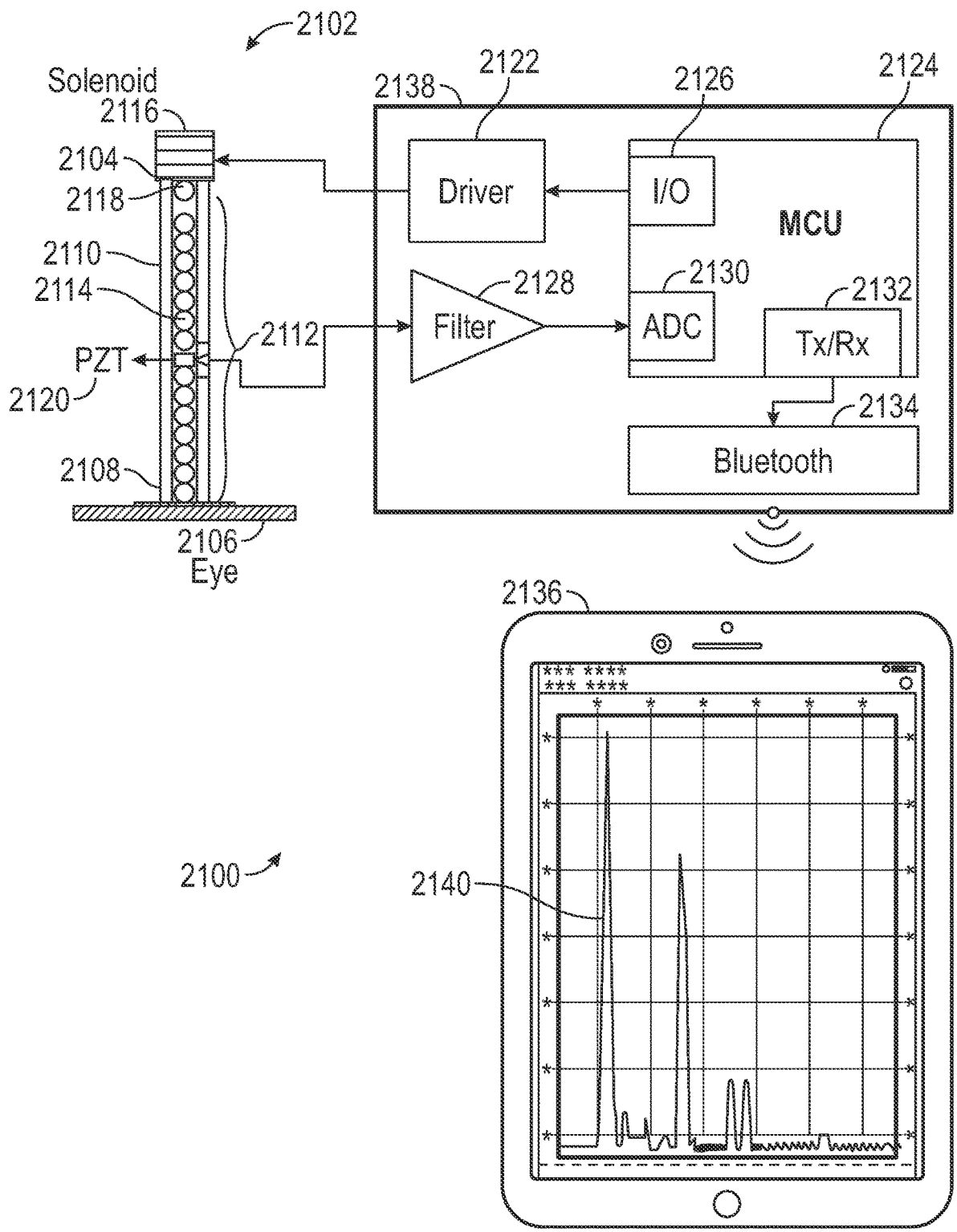
FIG. 21 is a schematic of another example tonometer with wireless communication.

FIG. 21 shows another example of a tonometer 2100 configured to operate wirelessly in part. Some examples can include features from examples described in the article "Wireless Module for Nondestructive Testing/Structural Health Monitoring Applications Based on Solitary Waves," by Misra, R., Jalali, H., Dickerson, S., and Rizzo, P., published May 26, 2020 in *Sensors*, 20, 3016. DOI:10.3390/s20113016, which is also incorporated by reference herein. The tonometer 2100 can include a transducer 2102 configured to produce solitary waves at a first end 2104 of the transducer 2102 and to direct the solitary waves to an eye 2106 (or eyelid) in solitary wave communication with a second end 2108 of the transducer 2102. In some examples, the transducer 2102 includes a frame 2110 supporting an array 2112 of particles 2114 which can be configured in a series to transmit the solitary waves in forward and reverse directions along the array 2112. In particular examples, the transducer 2102 includes a solenoid 2116 at the first end 2104 configured to suspend a striker particle 2118 at a selected height and to release the striker particle 2118 to strike the array 2112 and cause a solitary wave to propagate along the array 2112 toward the eye 2106. It will be appreciated that other striking mechanisms may be used, including springs or other resilient members configured to release energy to the array 2112 to induce the solitary waves. Combinations of mechanical and electrical components may be used in some examples, such as electromagnets and springs. After reaching the eye, a return solitary wave is formed and propagates from the second end 2108 back along the array 2112. A sensor 2120, such as a piezoelectric transducer, is situated within the array 2112 to detect solitary waves propagating passed, e.g., embedded within a particle or as a separate type of particle. In free-fall and other striker examples, the mass of the striker, such as the striker particle 2118, can be equal to the mass of the other particles 2114 of the array 2112, thereby producing a single solitary wave pulse.

In a particular example, the particles 2114 of the array 2112 include a plurality of non-ferromagnetic spheres with the striker particle 2118 being ferromagnetic. The solenoid 2116 can be configured to translate the striker particle 2118 to the selected height above the array 2112 and to release the striker particle 2118 upon cessation or interruption of the current through the solenoid 2116 so that the striker particle 2118 impacts the first particle of the array 2112 to form a solitary wave. In the particular example, the sensor 2120 includes a lead zirconate titanate (Pb[ZrxTi1-x]O3) wafer transducer (PZT) embedded between a pair of metal disks having a diameter similar to the particles 2114. For metal disk examples, the PZT can be insulated with an insulation layer. In some examples, the combined mass of the PZT and disks can be the same as one of the particles 2114.

A driver 2122, such as a current source or other controllable driving source, is coupled to the solenoid 2116 so as to controllably provide current to the solenoid 2116 for controllable generation of solitary waves. The driver 2122 can be coupled to a microcontroller (MCU) 2124 through an I/O port 2126 (such as general purpose I/O (GPIO)) and the MCU 2124 can be configured with instructions to control the initiation, repetition rate, repetitions, and other characteristics of the solitary waves generated by driving the solenoid 2116 with the driver 2122. The solitary waves propagating along the array 2112 can be detected by the sensor 2120 and the sense signal produced can be directed to an analog filter 2128 and the filtered signal can be subsequently sampled by an analog to digital converter (ADC) 2130 which is typically a component part of the MCU 2124. In some wireless examples, the MCU 2124 can then send the solitary wave data samples through communication port 2132 to an integrated circuit (IC) 2134 enabled for, e.g., Bluetooth Low Energy (BLE) communication using the Universal Asynchronous Receiver/Transmitter (UART) protocol. The protocol can allow for the wireless transmission of the solitary wave data to another computing device 2136 capable of BLE communication, such as a handheld mobile device, laptop, tablet, etc. In some examples, the computing device 2136 is wireless coupled to transmit solitary wave commands to the MCU 2124. In some examples, the computing device 2136 can be configured to display solitary waves 2140 or other information, such as intraocular pressure associated with the solitary wave data. In some wireless examples, the driver 2122, filter 2128, MCU 2124, and Bluetooth IC 2134 are arranged together on a printed circuit board (PCB) 2138. The PCB 2138 can be coupled to the transducer 2102 (e.g., solenoid 2116 and sensor 2120) through wired communication either through an extended wire or close together, such as within the frame 2110 of the transducer 2102. In other examples, different arrangements of wired and wireless communication can be provided, such as providing wireless communication between the driver 2122 and the MCU 2124, between the sensor 2120 and the filter 2128, and/or between the filter 2128 and the MCU 2124. In some examples, the MCU 2124 can be integrated into or form part of the computing device 2136 which can eliminate wireless communication between the MCU 2124 and the computing device 2136.

Figure 22:
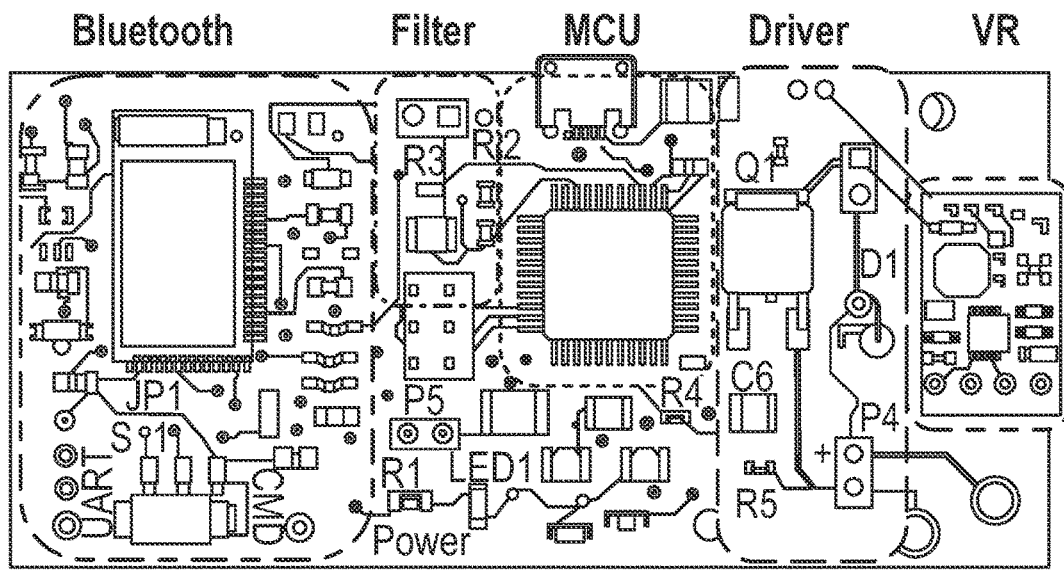
FIG. 22 is a labeled image of an example printed circuit board.

In a particular example shown in FIG. 22, the PCB 2138 had a form factor of 76.2×36.8 mm$^2$ and provided a substantially smaller footprint than earlier examples and provided enhanced portability. As shown in FIG. 22, the PCB 2138 includes a Bluetooth transceiver, a filter, an MCU, and a voltage regulator (VR). The MCU 2124 was an ATMega32u4 with 32 kB of flash memory for storing embedded programs, 2 kB of SRAM for storing measurement data, peripherals sufficient to induce and measure the solitary wave signal, and libraries that allowed for easy communication with the Bluefruit LE module. The MCU 2124 included a universal serial bus (USB) controller, allowing for local data collection without an additional an integrated circuit to perform FTDI to UART conversion. The size of further examples can be substantially reduced further such that the PCB 2138 or related driving and sensing components can be packaged with the transducer 2102 to form a singular handheld device with various capabilities. For example, some examples can control and store measurement data, with some examples allowing accessibility and/or display of the measurement data by a separate computing device, such as a mobile device, laptop, tablet, etc. Some examples can control, store, and display measurement data, with or without accessibility by a separate computing device.

In some examples, actuation can be effected with power supplied by batteries rather than through a bulky external power supply. In some examples, DC current used to drive the electromagnet of the solenoid 2116 can be supplied through the PCB 2138. Similar to some wired examples, in a wireless example the solenoid 2116 is energized for 250 ms, which corresponds to an interval of sufficient duration to lift the striker particle 2118 until it touches the electromagnet before falling freely onto the array 2112. The energy necessary to deliver the current necessary to operate the electromagnet is significant with respect to the other electronic components of the tonometer 2110 and is directly proportional to the weight and the falling height of the striker particle 2118. To supply the necessary energy, an example power source for the solenoid and driver circuit allows the control of the striker while maintaining portability. For example, LiPo, Li-Ion, or other suitable energy dense batteries may be used to provide a sufficient discharge rate and storage capacity for solitary wave IOP measurements. Shorter duration and/or smaller energy consumptions can be obtained by decreasing the falling height of the striker, by making the striker lighter (in order to be able to use smaller solenoids), or by minimizing the friction between the striker and the inner wall of the guide, by way of example.

Figure 23:
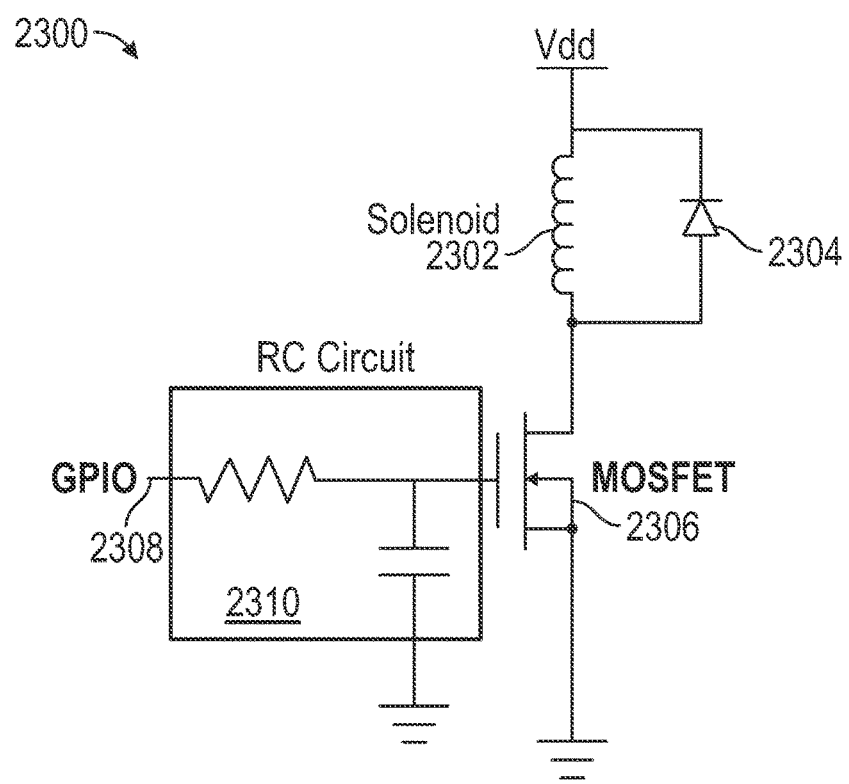
FIG. 23 is a schematic of an example control circuit.

FIG. 23 shows an example control circuit 2300 for providing actuation of a solenoid 2302, which can be used with various examples herein including the driver 2122 tonometer 2100. A 1N4003 diode 2304 was added in parallel to the solenoid 2302, which operates as a flyback diode that prevents a voltage spike resulting from turning off the solenoid, from damaging a metal—oxide—semiconductor field-effect transistor (MOSFET) 2306, which might otherwise reduce product lifespan and reliability. The MOSFET 2306 operates as an open circuit with a GPIO pin 2308 (or other control circuit input) in an off state, and operates as a closed circuit with the GPIO pin 2308 in an on state, allowing for the control of the current through the solenoid 2302 via, e.g., software. In an example, the MOSFET 2306 was an NTD3055-150 from ON Semiconductor, which is configured to operate in low voltage, high-speed switching applications in power supplies, converters and power motor controls and bridge circuits. An RC circuit 2310 at the gate of the transistor 2306 provides a slight delay between turning the GPIO pin 2308 off in software and the moment at which a magnetic striker particle on top of a tonometer chain drops. Various resistor and capacitor values may be used to adjust the time constant of the RC circuit 2310. In representative examples, the time constant is selected to be at least three times larger than the minimum delay that an MCU and/or related electronics can produce. This prevents an undesirable scenario where the MCU samples an ADC after an incident solitary wave passes the sensor configured to detect the wave. The delay introduced by the RC circuit 2310 also safeguards against similar detection failures where mechanical adjustments to the transducer are made that can reduce the amount of time it takes for the striker to fall. In one example, the RC circuit 2310 consisted of a 10 kΩ resistor and a 33 nF capacitor, resulting in a time constant of 333 µs.

In representative examples, the filter 2128 can be selected as a passive low-pass filter that can be used to remove white noise and provide anti-aliasing. The cutoff frequency can be determined by examining the frequency spectrum of solitary waves recorded at a selected sampling rate (such as 2 MHz) by placing a transducer above various surfaces. In one example, a 12.7 mm thick steel plate was used. Example filters can provide a cutoff frequency at a frequency selected to provide noise rejection as well as to retain significant solitary wave information. Such a cutoff frequency position can also serve to provide antialiasing. Example cutoff frequencies can include 10 kHz, 50 kHz, 100 kHz, 500 kHz, 1 MHz, 2 MHz, 10 MHz, 100 MHz, etc. In an example, the components of the 2128 filter have values equal to 2Ω and 33 nF, resulting in a cutoff frequency of 2.411 MHz. However, it will be appreciated that the filter and related characteristics can be modified based upon further refinements of the application of the solitary waves to tonometry, including variations in the characteristics of transducers, electronic componentry, the particles in the array, the properties of the eye (including intervening elements such as an eyelid) to be monitored, and the duration of the incident and reflected waves.

While the PCB 2138 discussed above uses a Bluetooth module and associated communication protocol for communication between the tonometer MCU 2124 and the external mobile device 2136, it will be appreciated that other wireless protocols may be used. For short-distance communication, Bluetooth protocol is beneficial in view of its compatibility with a substantial variety of electronic devices, including consumer devices such as smartphones, tablets, and laptops. Additionally, Bluetooth communication does not rely on any external network. In typical examples, the Bluetooth LE UART module relies on the general-purpose, ultra-low power System-on-Chip nrF51822 to provide wireless communication with any BLE-compatible device. The term "System-on-Chip" means that the nrF51822 is a complete computer system within a single chip that can act independently from the MCU. This capability can allow for improvements to future iterations of the PCB 2138. The nrF51822 has the ability to choose between UART and SPI communication with external devices, and sleep modes for power preservation.

Figure 24A:
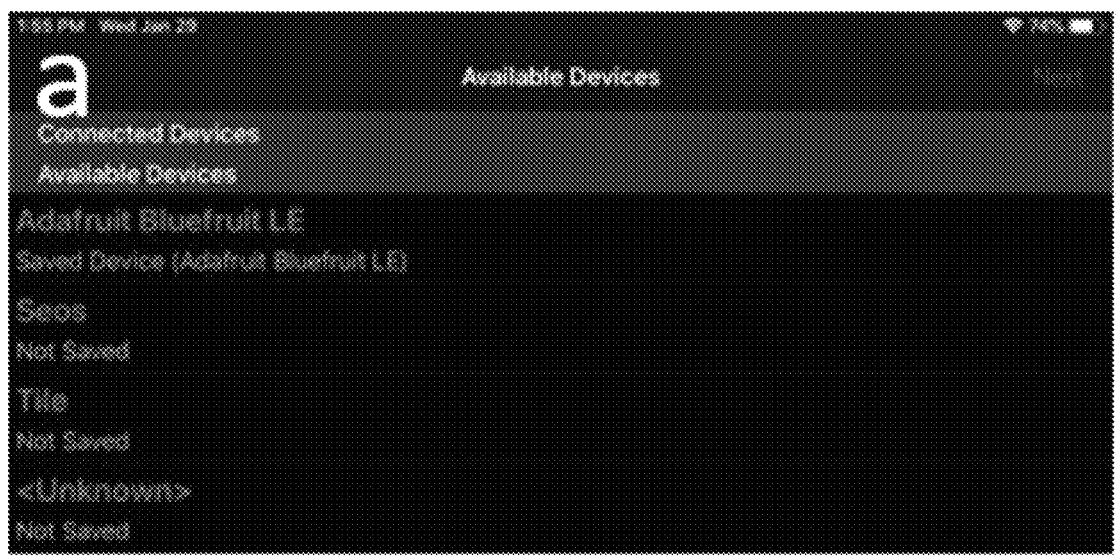
FIGS. 24A-24D are screenshots of a solitary wave tonometry software application user interface.
Figure 24B:
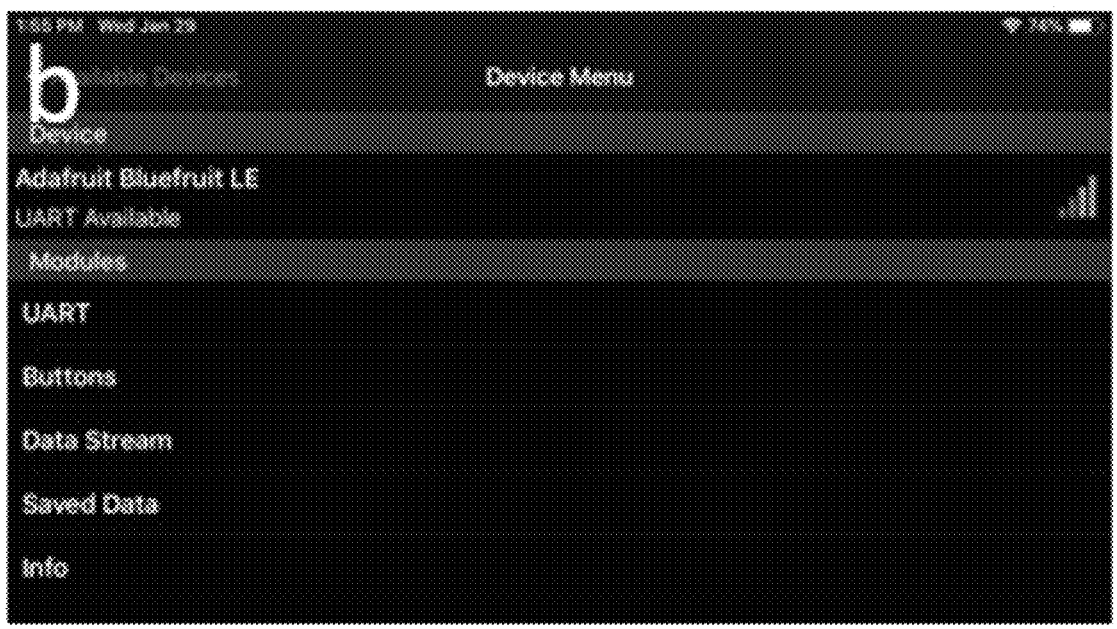
Figure 24C:
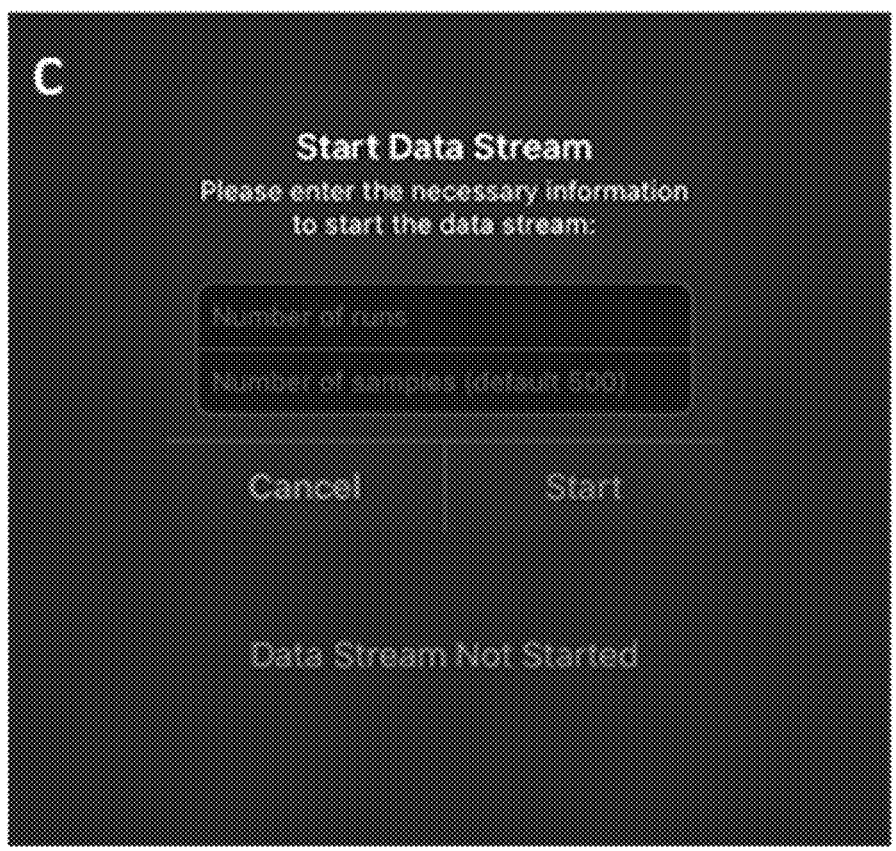
Figure 24D:
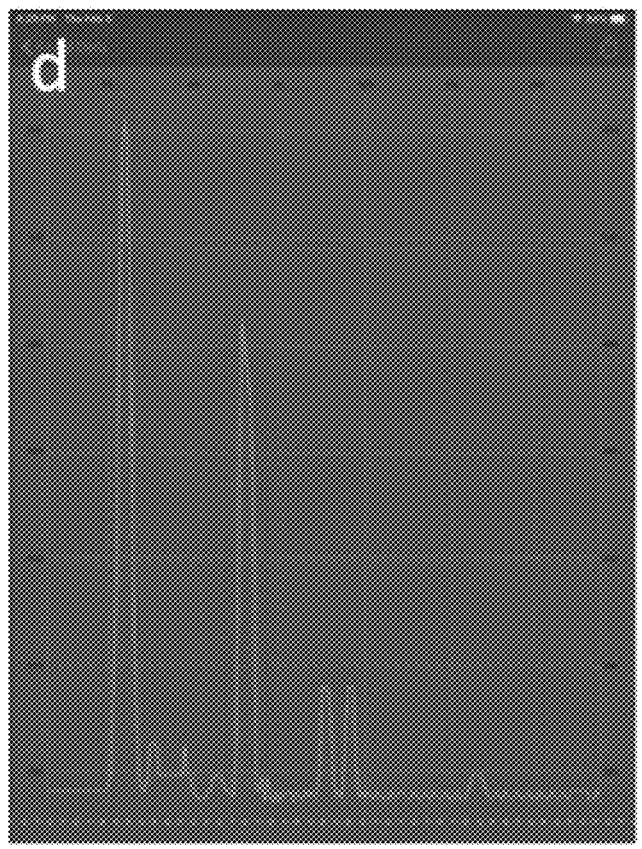

FIGS. 24A-24D show screenshots of an example user interface for an example software application configured for mobile devices, such as the computing device 2136. The software application was designed so that the mobile device can communicate with the transducer 2102 of the tonometer 2100 via the PCB 2138. The software application was adapted from a general application framework and customized by added a data streaming mode capable of compartmenting the data it received from different solitary wave runs into separate graphs. These plots can also be exported as data files for further processing. The data streaming was designed to work with the messaging protocol programmed into the MCU 2124. In representative examples, the software provides a list of Bluetooth devices within the vicinity. After the user selects the appropriate device (FIG. 24A), the "Data Stream" menu option allows the user to remotely drive the striker of the tonometer 2110 and to collect data from the embedded sensor disk (FIG. 24B). As shown in FIG. 24C, selecting a "Data Stream" option prompts the user to select the number of strikes and the length (data points) of the signal. After the PCB 2138 receives the command, it actuates the transducer 2102, collects samples of the time waveform from the ADC 2130, sends the data to the mobile device 2136, and iterates the process as many times as the number of strikes chosen by the user. During the process, the waveforms are displayed in real-time on the smart device (FIG. 24D). The software application and the 2138 PCB together can define a self-contained tonometry system that only requires a basic knowledge of smart mobile devices to operate.

In a particular implementation of the tonometer 2100, the ADC 2130 within the AtMega32u4 was used to digitize the signals detected by the embedded sensor disk 2120. The clock of the ADC 2130 was set equal to 1 MHz, as setting the clock to a higher frequency would reduce the resolution for this particular device. A single conversion takes 13 clock cycles, and the clock frequency was set to 16 MHz, so the highest theoretically achievable sampling frequency was 1 (MHz)/13=77 kHz. The ADC 2130 uses a sample-hold capacitor, which is first charged by the signal and then closed-off from the input signal so that the voltage of the signal at that time can be indirectly read through the voltage on the capacitor at that moment. A 5 V power supply for the ATMega32u4 and the Bluetooth module was generated with a 3.7 V single-cell LiPo and a Pololu 5 V Step-Up Voltage Regulator U1V11F5. The U1V11F5 can handle input voltages in a range of 1 to 5.5 V, so it is robust to small voltage drops caused by the discharging of the single-cell LiPo. The PCB 2138 follows a protocol for collecting data and sending the data wirelessly to the computing device 2136. After the first time the PCB 2138 is turned on, it waits for a mobile device to connect to it. After a device has connected, the PCB 2138 turns the solenoid 2116 on and off again, starts a timer, and then collects samples from the ADC 2130 until the ADC 2130 reading passes a certain threshold. This allows the PCB 2138 to learn the timing between the dropping of the striker particle 2104 and observing a HNSW. It then allows the wirelessly coupled computing device app to send to the PCB 2138 the desired number of samples and runs after which it executes the appropriate number of runs while recording the desired number of samples in time for each run. In some examples, IOP measurements and related data can be computed and displayed on the computing device 2136 after completion of the test.

General Considerations

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest," "best," "minimum," or the like. It will be appreciated that such descriptions are intended to indicate that a selection among many used functional alternatives can be made, and such selections need not be better, smaller, or otherwise preferable to other selections.

Algorithms may be, for example, embodied as software or firmware instructions carried out by one or more digital computers. For instance, any of the disclosed solitary-wave tonometry techniques can be performed by a computer or other computing hardware (e.g., an ASIC or FPGA) that is part of a tonometry system. The tonometry system can be connected to or otherwise in communication with the solitary wave detector and be programmed or configured to receive detected solitary wave characteristics and perform intraocular pressure measurement and estimate computations (e.g., any of the tonometry techniques disclosed herein). The computer can be a computer system comprising one or more processors (processing devices) and tangible, non-transitory computer-readable media (e.g., one or more optical media discs, volatile memory devices (such as DRAM or SRAM), or nonvolatile memory or storage devices (such as hard drives, NVRAM, and solid state drives (e.g., Flash drives)). The one or more processors can execute computer-executable instructions stored on one or more of the tangible, non-transitory computer-readable media, and thereby perform any of the disclosed techniques. For instance, software for performing any of the disclosed embodiments can be stored on the one or more volatile, non-transitory computer-readable media as computer-executable instructions, which when executed by the one or more processors, cause the one or more processors to perform any of the disclosed tonometry techniques. The results of the computations can be stored (e.g., in a suitable data structure or lookup table) in the one or more tangible, non-transitory computer-readable storage media and/or can also be output to the user, for example, by displaying, on a display device (such as a display on the housing of a device directing the solitary wave to the eye or remotely on a mobile device or other display), detected wave characteristics or intraocular pressures with a graphical user interface.

Having described and illustrated the principles of the disclosed technology with reference to the illustrated embodiments, it will be recognized that the illustrated embodiments can be modified in arrangement and detail without departing from such principles. For instance, elements of the illustrated embodiments shown in software may be implemented in hardware and vice-versa. Also, the technologies from any example can be combined with the technologies described in any one or more of the other examples. It will be appreciated that procedures and functions such as those described with reference to the illustrated examples can be implemented in a single hardware or software module, or separate modules can be provided. The particular arrangements above are provided for convenient illustration, and other arrangements can be used.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. We therefore claim all that comes within the scope of the appended claims.

We claim:

1. An apparatus, comprising:
   a particle array configured to propagate an incident solitary wave to an eye;
   a housing configured to support the particle array;
   a sensor coupled to the particle array and configured to detect a return solitary wave propagating along the particle array from the eye; and
   a membrane attached to the housing, and configured to removably contact an eyelid of the eye to couple the particle array to the eye.

2. The apparatus of claim 1, wherein the particle array comprises a plurality of adjacently arranged loosely coupled particles that propagate the incident and return solitary waves from one particle to a next particle.

3. The apparatus of claim 2, further comprising a particle array compressive member coupled to at least one of the particles of the particle array to provide a compression for the particle array that contact among the particles.

4. The apparatus of claim 2, wherein the housing includes a bend defining a bent path for the particle array arranged such that a weight of a plurality of the particles along a portion of the bent path compress the particles to provide the loose coupling.

5. The apparatus of claim 2, wherein the particles have spherical, cylindrical, or elliptical shape, or a mix of shapes, and are made of Polytetrafluoroethylene (PTFE), steel, or another material having an elastic modulus between 0.01 and 200 GPa.

6. The apparatus of claim 2, wherein the sensor comprises a magnetic coil encircling at least a portion of at least one of the particles or a piezoelectric transducer embedded in at least one of the particles.

7. The apparatus of claim 1, wherein the sensor comprises a stress wave sensor.

8. The apparatus of claim 1, further comprising a solitary wave actuator coupled to the particle array and configured to produce the incident solitary wave in the particle array.

9. The apparatus of claim 8, further comprising:
driving circuitry configured to drive the actuator wherein the driving circuitry includes delay circuitry configured to reduce a sampling error; and
filter circuitry configured to filter solitary wave data detected by the sensor.

10. The apparatus of claim 9, further comprising wireless transmission circuitry configured to wirelessly transmit the filtered solitary wave data to a separate computing device.

11. The apparatus of claim 8, wherein the actuator comprises a solenoid configured to raise a striker particle and to drop the striker particle from a height.

12. The apparatus of claim 8, further comprising:
a function generator coupled to the actuator and configured to generate an incident solitary wave signal for the actuator;
an analog to digital converter coupled to the sensor and configured to digitize the detected return solitary wave to form a digitized return solitary wave signal;
a processor coupled to the analog to digital converter and function generator; and
a memory coupled to the processor and configured with instructions executable by the processor for controlling the production of the incident solitary wave in the particle array.

13. The apparatus of claim 12, wherein the memory is further configured with the instructions for determining an intraocular pressure of the eye based on one or more characteristics of the digitized return solitary wave signal.

14. The apparatus of claim 12, further comprising a wireless communication circuit coupled to the processor and configured to communicate data describing the digitized return solitary wave signal to an external signal processing device.

15. A method, comprising:
directing an incident solitary wave along a solitary wave particle array coupled to an eyelid of an eye through a membrane attached to a housing supporting the solitary wave particle array, wherein the membrane is configured to removably contact the eyelid of the eye to couple the particle array to the eye; and
detecting at least one return solitary wave propagating along the solitary wave particle array from the eye with a sensor coupled to the particle array.

16. The method of claim 15, further comprising producing an intraocular pressure estimate of the eye by comparing detected characteristics of the return solitary wave to characteristics of the incident solitary wave.

17. The method of claim 16, wherein the comparing includes comparing a stored relationship between (i) a time of return solitary wave time of flight and/or a ratio of incident and detected wave amplitudes and (ii) intraocular pressure.

18. A computer-readable medium including stored instructions which, when executed by one or more processors coupled to a solitary wave tonometer, wherein the tonometer includes a particle array configured to propagate an incident solitary wave to an eye, a housing configured to support the particle array, a sensor coupled to the particle array and configured to detect a return solitary wave propagating along the particle array from the eye, and a membrane attached to the housing, and configured to removably contact an eyelid of the eye to couple the particle array to the eye, cause the one or more processors to produce an intraocular pressure estimate for the eye by comparing stored solitary wave data describing a tonometer detection event of the eye including return solitary wave data to a stored relationship between (i) solitary waves and (ii) intraocular pressure.

19. The computer readable medium of claim 18, further comprising stored instructions causing the one or more processors: to direct an actuator to produce the incident solitary wave along the solitary wave particle array coupled to the eye, and to store the solitary wave data including data from a detection signal received in response to the actuating.

20. An apparatus, comprising:
a particle array configured to propagate an incident solitary wave to an eye;
a housing configured to support the particle array;
a sensor coupled to the particle array and configured to detect a return solitary wave propagating along the particle array from the eye;
a solitary wave actuator coupled to the particle array and configured to produce the incident solitary wave in the particle array;
driving circuitry configured to drive the actuator wherein the driving circuitry includes delay circuitry configured to reduce a sampling error; and
filter circuitry configured to filter solitary wave data detected by the sensor.

21. An apparatus, comprising:
a particle array configured to propagate an incident solitary wave to an eye;
a housing configured to support the particle array;
a sensor coupled to the particle array and configured to detect a return solitary wave propagating along the particle array from the eye;
a solitary wave actuator coupled to the particle array and configured to produce the incident solitary wave in the particle array;
a function generator coupled to the actuator and configured to generate an incident solitary wave signal for the actuator;
an analog to digital converter coupled to the sensor and configured to digitize the detected return solitary wave to form a digitized return solitary wave signal;
a processor coupled to the analog to digital converter and function generator; and
a memory coupled to the processor and configured with instructions executable by the processor for controlling the production of the incident solitary wave in the particle array.

* * * * *